United States Patent
Kamee et al.

(10) Patent No.: US 10,729,312 B2
(45) Date of Patent: Aug. 4, 2020

(54) ENDOSCOPE LIGHT SOURCE DEVICE AND ENDOSCOPE DEVICE

(71) Applicant: OLYMPUS CORPORATION, Tokyo (JP)

(72) Inventors: Hiroyuki Kamee, Koganei (JP); Eiji Yamamoto, Musashimurayama (JP); Takeshi Ito, Hino (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/707,054

(22) Filed: Dec. 9, 2019

(65) Prior Publication Data

US 2020/0107706 A1 Apr. 9, 2020

Related U.S. Application Data

(63) Continuation of application No. PCT/JP2017/021514, filed on Jun. 9, 2017.

(51) Int. Cl.
| | |
|---|---|
| *A61B 1/00* | (2006.01) |
| *A61B 1/06* | (2006.01) |
| *A61B 1/07* | (2006.01) |
| *G02B 27/48* | (2006.01) |

(52) U.S. Cl.
CPC ........ *A61B 1/00167* (2013.01); *A61B 1/0638* (2013.01); *A61B 1/07* (2013.01); *G02B 27/48* (2013.01)

(58) Field of Classification Search
CPC ....... A61B 1/00163–00197; A61B 1/06–0692; A61B 1/07; G02B 27/48
See application file for complete search history.

(56) References Cited

U.S. PATENT DOCUMENTS

| | | |
|---|---|---|
| 2002/0001759 A1 | 1/2002 | Ohashi et al. |
| 2017/0209032 A1 | 7/2017 | Matsunobu et al. |

FOREIGN PATENT DOCUMENTS

| | | |
|---|---|---|
| CN | 102499615 A | 6/2012 |
| JP | 11-72905 A | 3/1999 |
| JP | 2009-168524 A | 7/2009 |

(Continued)

OTHER PUBLICATIONS

International Search Report dated Aug. 8, 2017 received in PCT/JP2017/021514.

(Continued)

*Primary Examiner* — Sean P Gramling
(74) *Attorney, Agent, or Firm* — Scully, Scott, Murphy & Presser, P.C.

(57) ABSTRACT

An endoscope light source device includes a light source to emit light, and a speckle reduction member to scatter the light. The reduction member has a surface including thickness variation to provide the light with an optical path difference. The device also includes a drive to move the reduction member, and a lens to condense the light passed through the reduction member onto a light guide of an endoscope. The surface of the reduction member has inclination of an average inclination angle. The average inclination angle is determined so that a light quantity loss rate of the entering light into the light guide by scattering of the reduction member and refraction of the lens has a positive value equal to or smaller than an effective allowable loss rate.

15 Claims, 15 Drawing Sheets

(56) References Cited

FOREIGN PATENT DOCUMENTS

JP    2015-223463 A    12/2015

OTHER PUBLICATIONS

Blase, B., "Compact Laser Illumination System for Endoscopic Interventions", Proceedings of the Annual International Conference of the IEEE Engineering in Medicine and Biology Society (EMBC 2015), 2015, vol. 37, No. 7, pp. 5875-5878, ISSN 1557-170X.

English translation of International Preliminary Report on Patentability dated Dec. 19, 2019, together with the Written Opinion received in related International Application No. PCT/JP2017/021514.

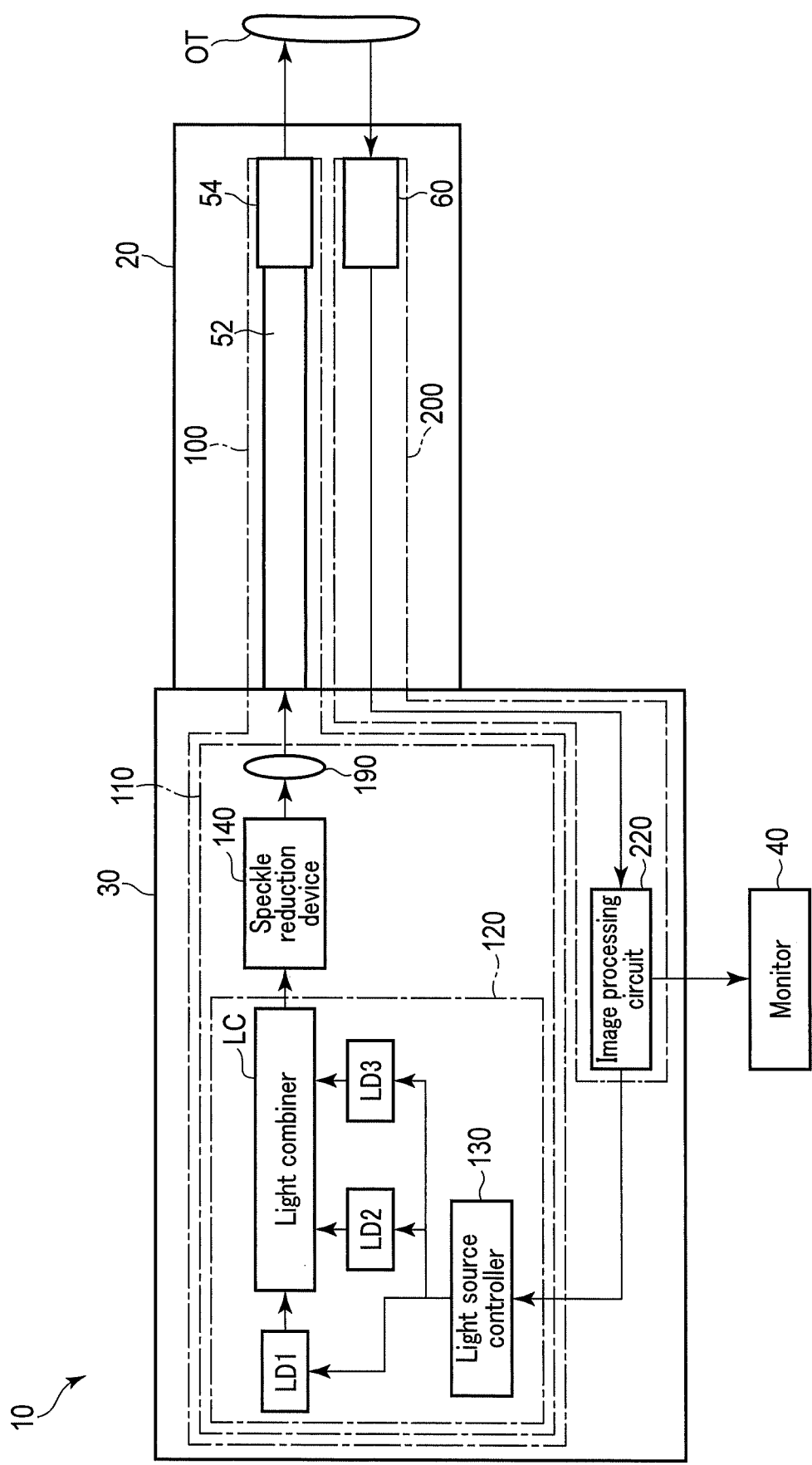
F I G. 2

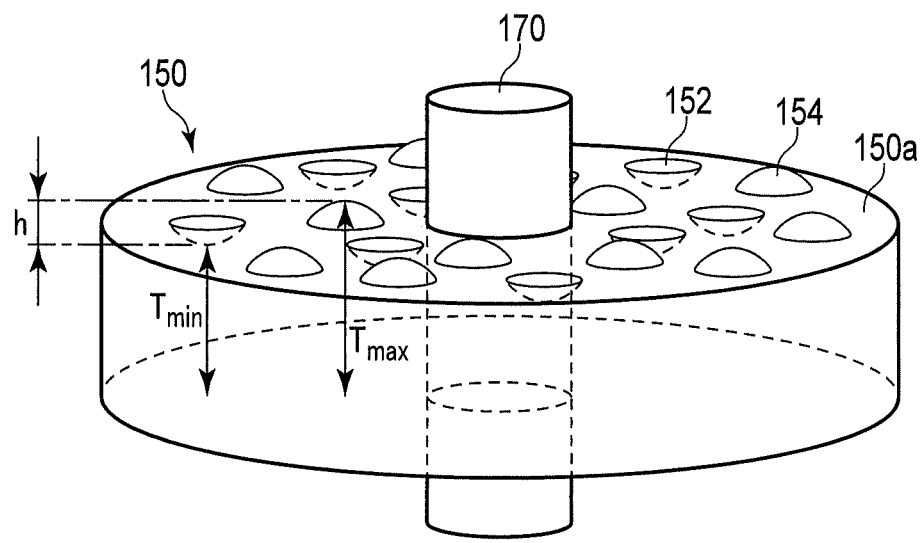
F I G. 4
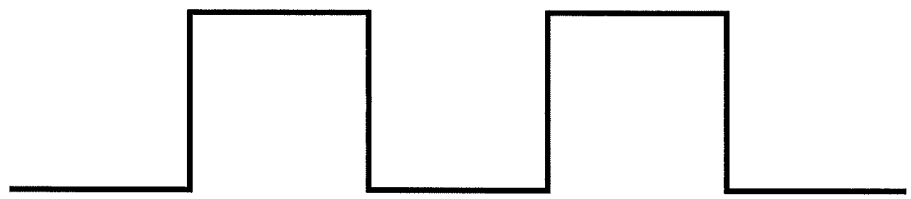
F I G. 5A
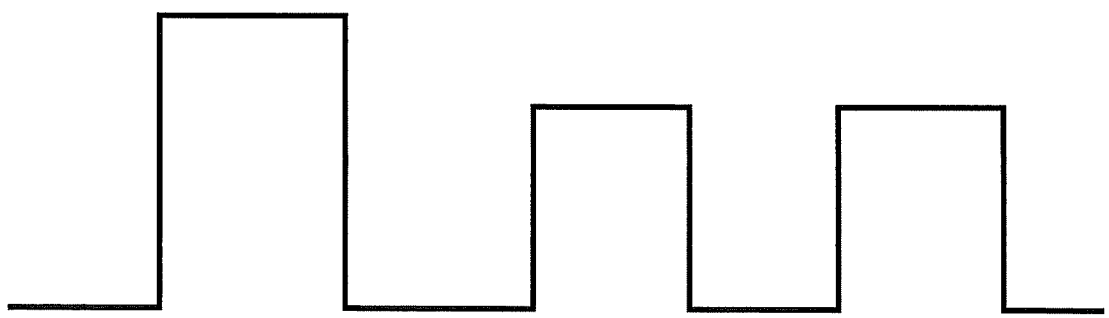
F I G. 5B

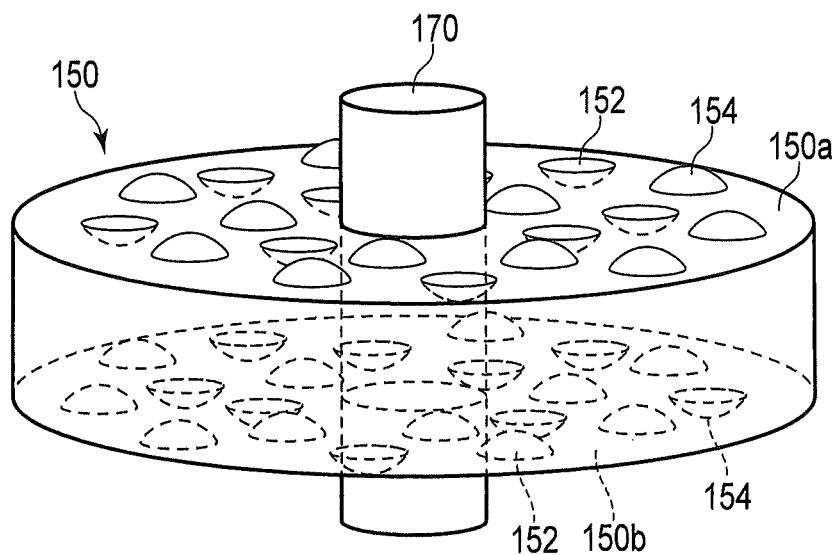
F I G. 6
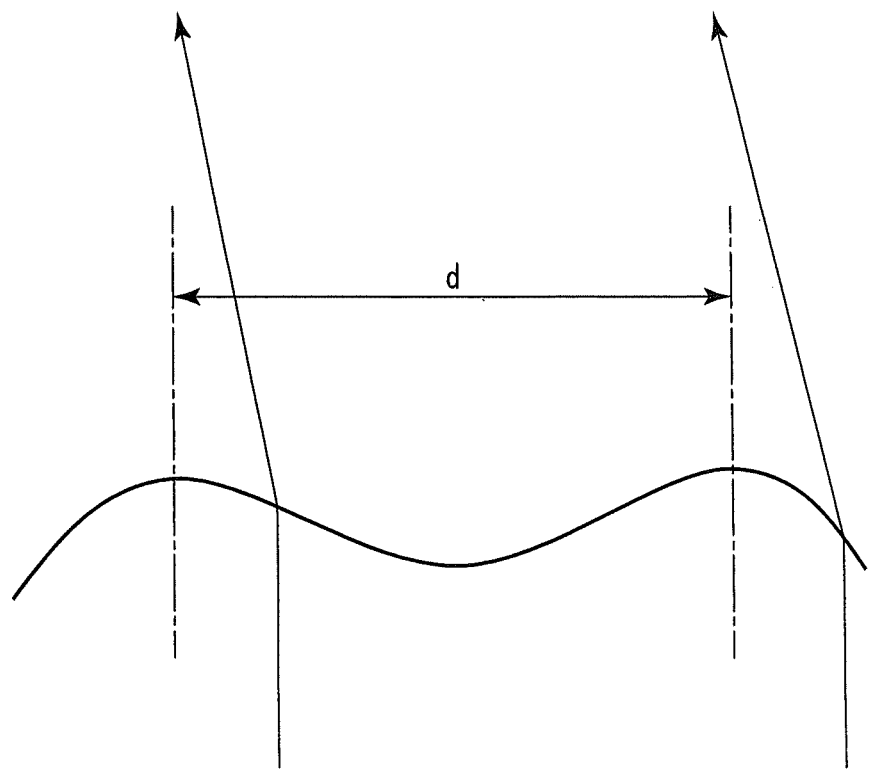
F I G. 7

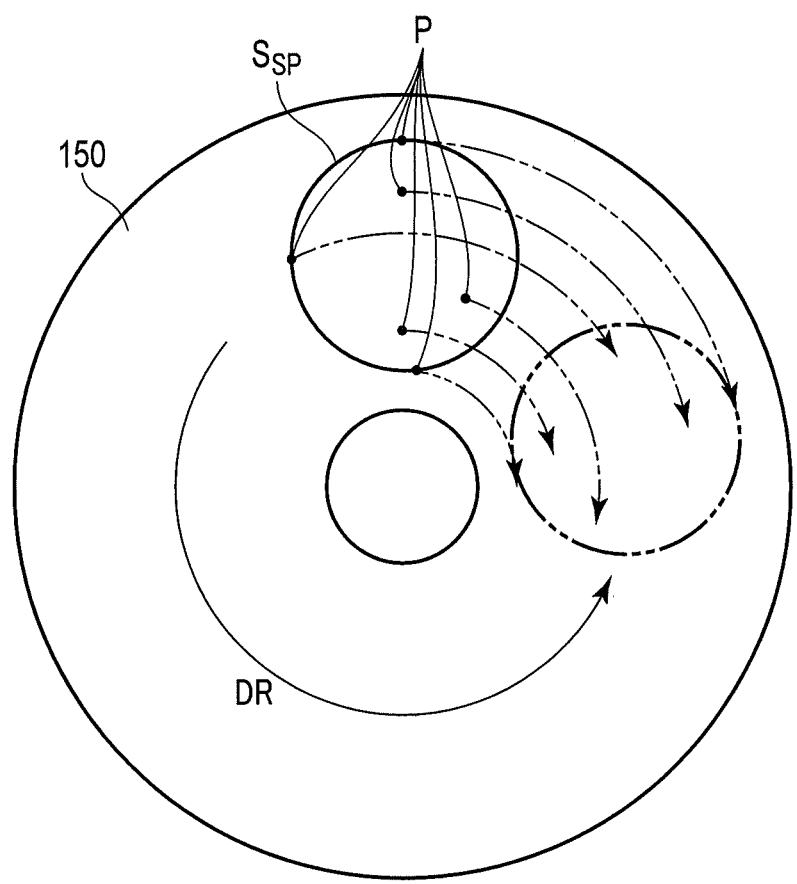
F I G. 16

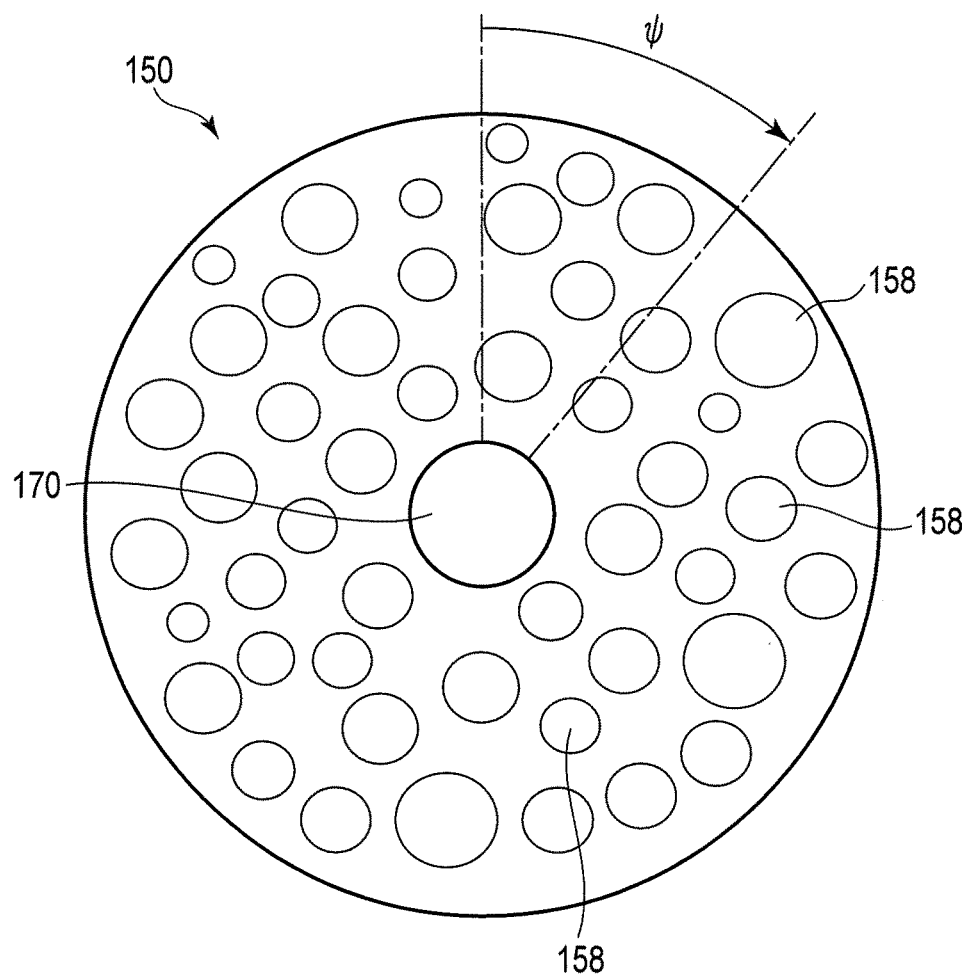
F I G. 18A
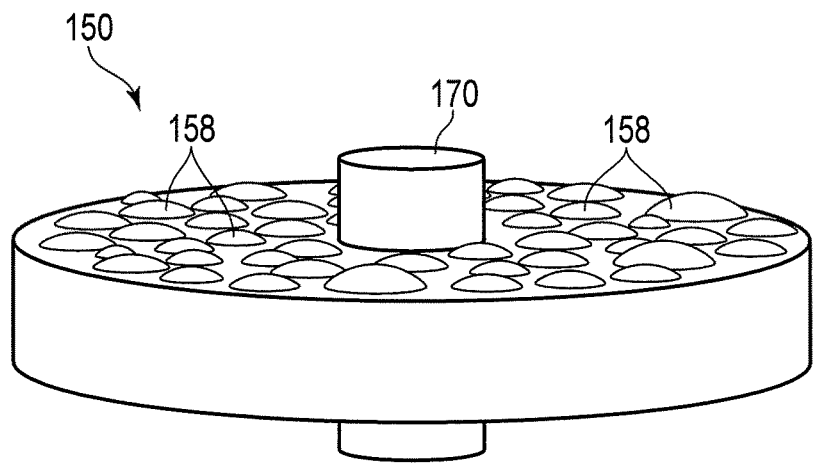
F I G. 18B

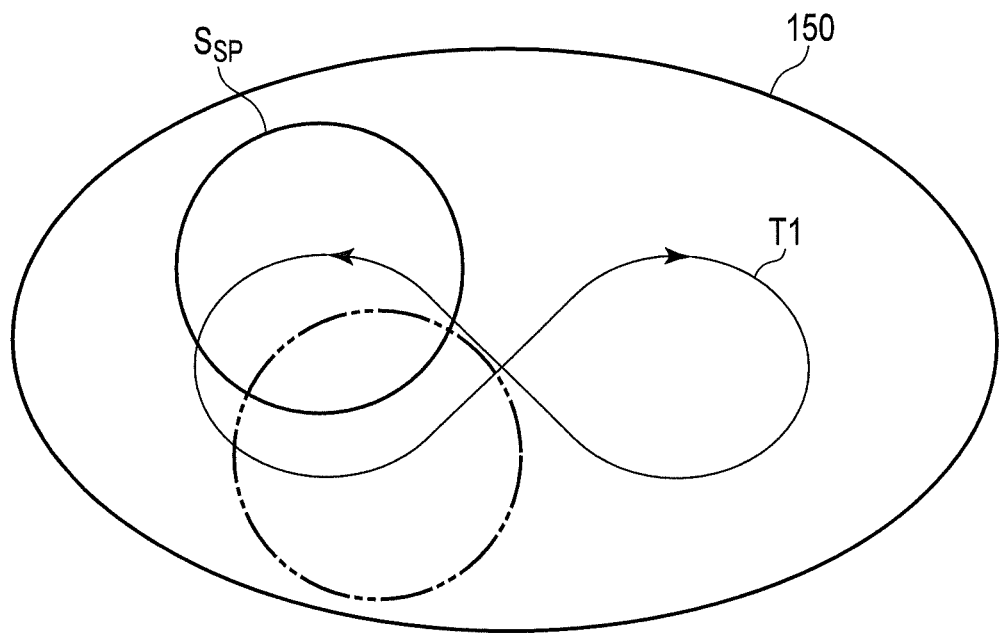
F I G. 19A
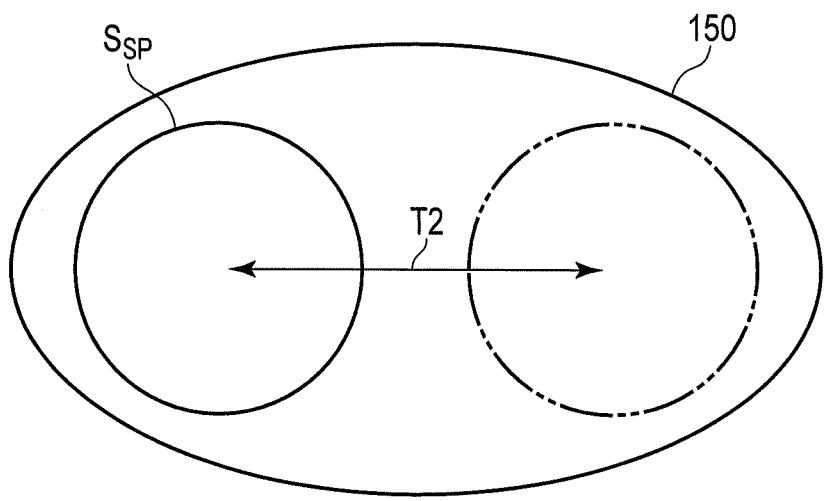
F I G. 19B

ENDOSCOPE LIGHT SOURCE DEVICE AND ENDOSCOPE DEVICE

CROSS-REFERENCE TO RELATED APPLICATIONS

This application is a Continuation Application of PCT Application No. PCT/JP2017/021514, filed Jun. 9, 2017, the entire contents of which are incorporated herein by reference.

BACKGROUND OF THE INVENTION

1. Field of the Invention

The present invention relates to an endoscope light source device used for an illumination device for an endoscope and an endoscope device.

2. Description of the Related Art

In recent years, development of illumination devices using semiconductor lasers have been actively proceeded. The illumination devices using the semiconductor lasers have merits, such as small size, high luminance, and low power consumption. By contrast, the illumination devices using the semiconductor lasers cause "speckles" due to high coherence of laser light.

Speckles are a phenomenon in which interference patterns reflecting the state around the surface of the observation target are generated in the observation image when light having high coherence, such as laser light, is applied to the observation target, because of overlapping of phases of light reflected and scattered by the surface of the observation target. Since speckles cause deterioration in image quality, techniques for reducing speckles have been developed.

A technique for reducing speckles is, for example, disclosed in Japanese Patent Application Publication No. 2015-223463. Japanese Patent Application Publication No. 2015-223463 is aimed at reducing speckle noise by a simple method and equalizing degrees of magnitudes of speckle noises observed in respective colors (wavelengths), and discloses an illumination device including at least one laser light source, an optical fiber that laser light emitted from the laser light source enters, and a diffusion member configured to generate secondary light by diffusing the laser light emitted from the optical fiber. In the illumination device, laser light enters an entrance end surface of the optical fiber in an oblique direction with respect to a normal stood on the entrance end surface.

BRIEF SUMMARY OF THE INVENTION

The present invention is directed to an endoscope light source device configured to emit light for illuminating an observation target through an endoscope to be connected thereto. The endoscope light source device includes a light source configured to emit light having a predetermined wavelength and coherence, and a speckle reduction member disposed to cross an optical path of the light emitted from the light source. The speckle reduction member is configured to scatter the entering light, and has a surface including thickness variation that provides the light with a speckle reduction valid optical path difference or more corresponding to the predetermined wavelength. The endoscope light source device also includes a driver configured to move the speckle reduction member, and a light condensing lens configured to condense the light that has passed through the speckle reduction member onto a light guide of the endoscope. The surface of the speckle reduction member including the thickness variation has inclination of a predetermined average inclination angle with respect to a plane perpendicular to an optical axis. The predetermined average inclination angle is determined so that a light quantity loss rate of the entering light into the light guide by scattering of the speckle reduction member and refraction of the light condensing lens has a positive value equal to or smaller than an effective allowable loss rate.

The present invention is also directed to an endoscope device. The endoscope device includes an endoscope including a light guide, and the above mentioned endoscope light source device.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 illustrates functional blocks of the endoscope system illustrated in FIG. 1;

FIG. 4 illustrates a speckle reduction member having projections and depressions in a surface thereof;

FIG. 5A illustrates a cross-sectional shape of thickness variation having projections and depressions having difference in level of a rectangular shape of only one type;

FIG. 5B illustrates a cross-sectional shape of thickness variation having projections and depressions having difference in level of rectangular shapes of a plurality of types;

FIG. 6 illustrates a speckle reduction member having projections and depressions in both a front surface and a back surface;

FIG. 7 illustrates a distance between close maximum thickness points that is a straight-line distance between two closest maximum thickness points;

FIG. 16 schematically illustrates relative movement of a speckle reduction member application region with respect to rotation of the speckle reduction member;

FIG. 18A is a plan view of the speckle reduction member having random projections and depressions;

FIG. 18B is a perspective view of the speckle reduction member illustrated in FIG. 17A;

FIG. 19A illustrates swing movement of the speckle reduction member applicable instead of rotation movement; and FIG. 19B illustrates shaking movement of the speckle reduction member applicable instead of rotation movement.

DETAILED DESCRIPTION OF THE INVENTION

[Endoscope System 10]

Figure 1:
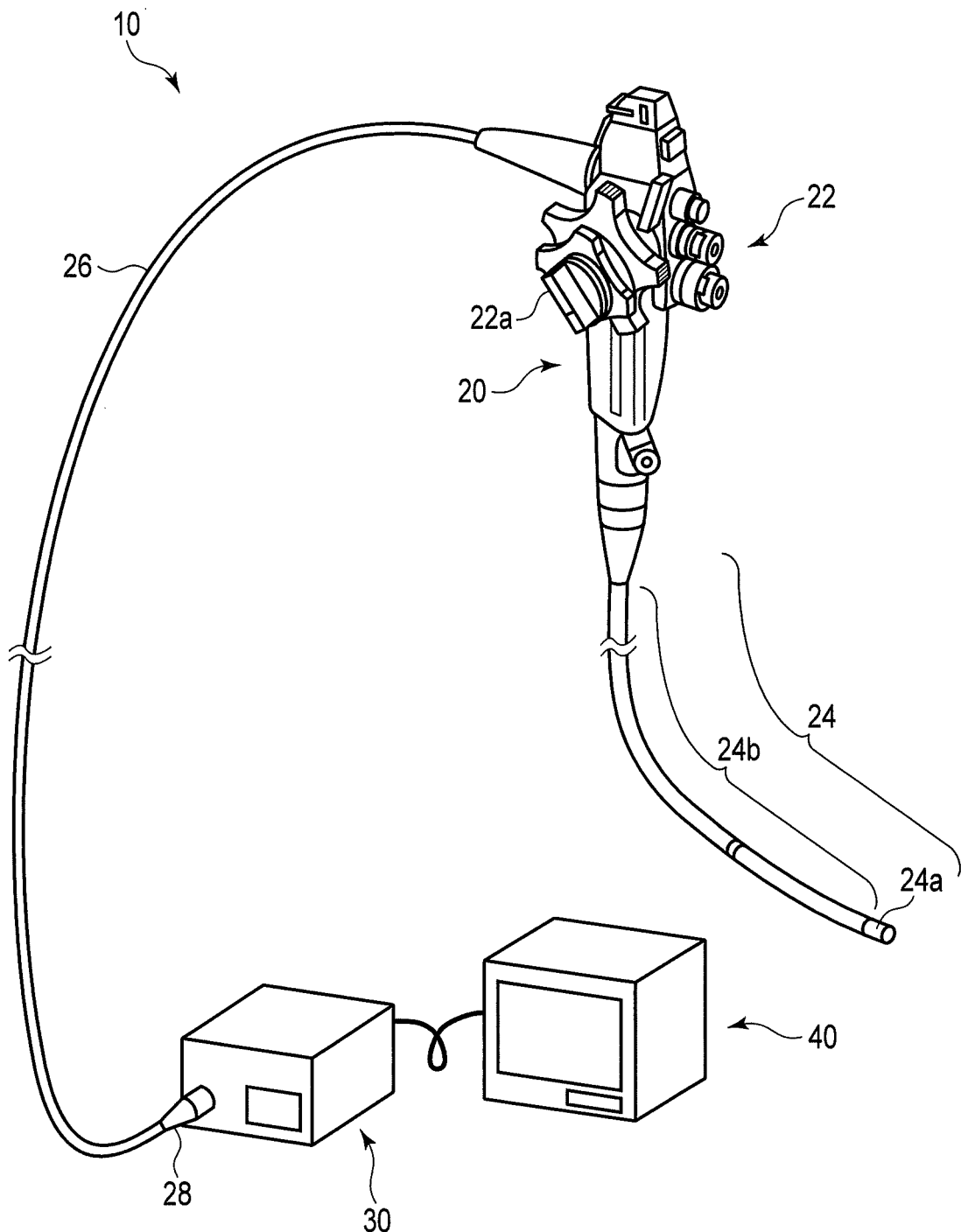
FIG. 1 illustrates an endoscope system according to a first embodiment.

FIG. 1 illustrates an endoscope system 10 according to the present embodiment. The endoscope system 10 includes an endoscope 20, an endoscope main member 30 to which the endoscope 20 is connected, and a monitor 40 connected to the endoscope main member 30.

The endoscope 20 includes a hollow elongated insertion section 24 to be inserted into a pore of the observation target, a control section 22 coupled with a proximal end section of the insertion section 24, and a universal cord 26 extending from the control section 22.

The insertion section 24 includes an insertion distal end section 24a configured to be hard, and an insertion bendable section 24b configured to be flexible. In this manner, the insertion bendable section 24b is configured to be passively bendable. For example, the insertion bendable section 24b is bent after the shape in the pore, when it is inserted into the pore of the observation target.

The control section 22 is provided with an operation handle 22a to bend the insertion section 24 in a vertical direction and/or a horizontal direction. The insertion section 24 is bent in the vertical direction and/or the horizontal direction by an operator's operation of the operation handle 22a. Specifically, the insertion section 24 is configured to be actively bendable.

The endoscope 20 is connected to the endoscope main member 30 through the universal cord 26. The universal cord 26 includes a connection section 28 attachable to and detachable from the endoscope main member 30. The connection section 28 functions as an interface of data transmitted and received between the endoscope 20 and the endoscope main member 30.

FIG. 2 illustrates functional blocks of the endoscope system 10 illustrated in FIG. 1. As illustrated in FIG. 2, the endoscope system 10 includes an illumination device 100 configured to illuminate the observation target OT, and an imaging device 20 configured to image the observation target OT.

The illumination device 100 includes a light source device 110 configured to emit light for illuminating the observation target OT, a light guide 52 configured to guide light emitted from the light source device 110, and a light emission unit 54 configured to emit the light guided by the light guide 52 to the outside of the endoscope 20.

The light source device 110 is disposed inside the endoscope main member 30. The light guide 52 extends inside the endoscope 20. Specifically, the light guide 52 extends from the connection section 28 attachable to and detachable from the endoscope main member 30, and extends to the insertion distal end section 24a through the inside of the universal cord 26, the control section 22, and the insertion section 24. The light guide 52 may be formed of, for example, a single-line optical fiber, or a bundle fiber formed by bundling a plurality of optical fibers. The light emission unit 54 is disposed at the insertion distal end section 24a, and optically connected to the light guide 52.

In other words, the light source device 110 constitutes the illumination device 100 in cooperation with the endoscope 20, more specifically, in cooperation with the light guide 52 and the light emission unit 54 in the endoscope 20.

The light emitted from the light source device 110 enters the light guide 52. The light that has entered the light guide 52 is guided by the light guide 52 and enters the light emission unit 54. The light that has entered the light emission unit 54 is emitted to the outside of the endoscope 20 by the light emission unit 54. The light emitted to the outside of the endoscope 20 is applied to, for example, the observation target OT. The light applied to the observation target OT is reflected and/or scattered by, for example, the observation target OT.

The imaging device 200 includes an imager 60 configured to acquire an optical image of the observation target OT illuminated by the illumination device 100, and an image processing circuit 220 configured to process an image signal of the optical image of the observation target OT acquired by the imager 60. The imager 60 is installed in the insertion distal end section 24a. The image processing circuit 220 is disposed inside the endoscope main member 30. The imager 60 is electrically connected to the image processing circuit 220 through an imaging cable or the like.

The image signal of the optical image of the observation target OT acquired by the imager 60 is supplied to the image processing circuit 220. The image processing circuit 220 performs necessary image processing on the supplied image signal, and supplies the image-processed image signal to the monitor 40. The monitor 40 displays an image in accordance with the supplied image signal. The monitor 40 may be formed of, for example, a liquid crystal display, although the monitor 40 is not limited thereto.

The light source device 110 includes a light source 120 configured to emit light having a predetermined wavelength. The light source 120 may emit light having a single wavelength, or emit light having a plurality of wavelengths. In the present embodiment, as an example, the light source 120 emits light having three wavelengths. For this reason, the light source 120 includes a first laser light source LD1, a second laser light source LD2, and a third laser light source LD3. In the structure, the wavelengths of light emitted from the respective laser light sources LD1, LD2, and LD3 are mutually different. For example, the laser light sources LD1, LD2, and LD3 are formed as follows. The laser light source LD1 is a blue laser light source configured to emit blue laser light having a center wavelength of 445 nm. The laser light source LD2 is a green laser light source configured to emit green laser light having a center wavelength of 532 nm. The laser light source LD3 is a red laser light source configured to emit red laser light having a center wavelength of 635 nm.

Each of the laser light sources LD1, LD2, and LD3 may be formed of, for example, a laser diode, although they are not limited thereto.

The light source 120 also includes a light source controller 130 configured to control driving of the laser light sources LD1, LD2, and LD3, and a light combiner LC configured to combine laser light emitted from the laser light sources LD1, LD2, and LD3.

The light source controller 130 adjusts the light quantities of the laser light sources LD1, LD2, and LD3 by acquiring and analyzing an image signal from the image processing circuit 220 so that, for example, the image of the observation target OT is displayed on the monitor 40 with proper brightness.

The light combiner LC combines the three beams of laser light emitted from the laser light sources LD1, LD2, and LD3 into a beam, and then emits the combined beam.

In addition to the light source 120, the light source device 110 includes a speckle reduction device 140 configured to reduce speckles generated when the light emitted from the light source 120 is applied to the observation target OT through the endoscope 20, and a light condensing lens 190 configured to course the light that has passed through the speckle reduction device 140 to enter the light guide 52 of the endoscope 20.

The light condensing lens 190 is schematically illustrated as a lens in FIG. 2, but may comprises a plurality of lenses.

Figure 3:
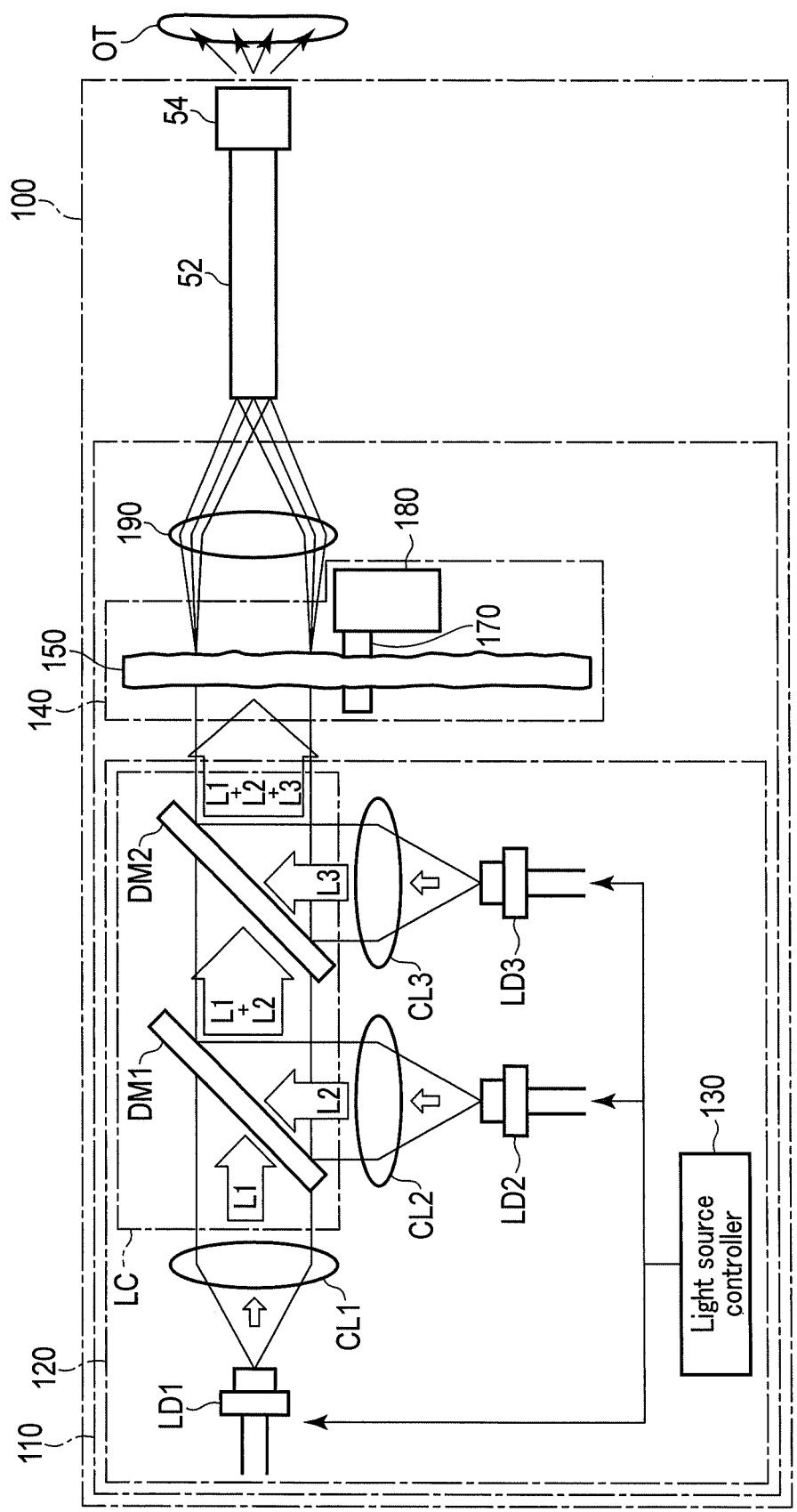
FIG. 3 further specifically illustrates a structure of a light source device illustrated in FIG. 2.

FIG. 3 further specifically illustrates the illumination device 100 illustrated in FIG. 2, in particular, the structure of the light source device 110. In particular, FIG. 3 schematically illustrates specific structures of the light combiner LC and the speckle reduction device 140.

Collimate lenses CL1, CL2, and CL3 configured to collimate respective beams of laser light L1, L2, and L3 emitted from the laser light sources LD1, LD2, and LD3 are disposed ahead of the laser light sources LD1, LD2, and LD3, respectively. In other words, the light source 120 includes collimate lenses CL1, CL2, and CL3 configured to collimate respective beams of laser light L1, L2, and L3 emitted from the laser light sources LD1, LD2, ad LD3.

The divergent beams of laser light L1, L2, and L3 emitted from the laser light sources LD1, LD2, and LD3 are collimated by the collimate lenses CL1, CL2, and CL3, respectively, that is, converted into parallel beams, and thereafter enters the light combiner LC.

The light combiner LC includes a dichroic mirror DM1 configured to transmit the laser light L1 emitted from the laser light source LD1 but reflect the laser light L2 emitted from the laser light source LD2, and a dichroic mirror DM2 configured to transmit the laser light L1 and L2 emitted from the laser light sources LD1 and LD2 but reflect the laser light L3 emitted from the laser light source LD3.

The dichroic mirror DM1 is disposed so that the beam of laser light L2 reflected by the dichroic mirror DM1 is combined with the beam of laser light L1 transmitted through the dichroic mirror DM1 with a common axis into a beam. The dichroic mirror DM2 is disposed so that the beam of laser light L3 reflected by the dichroic mirror DM2 is combined with the beams of laser light L1 and L2 transmitted through the dichroic mirror DM2 with a common axis into a beam.

The two beams of laser light L1 and L2 that has entered the light combiner LC are combined into a beam by the dichroic mirror DM1. The beam of laser light L1 and L2 combined by the dichroic mirror DM1 is further combined with the beam of laser light L3 that has entered the light combiner LC into a beam by the dichroic mirror DM2. The laser light L1, L2, and L3 that has been combined into the beam is thereafter emitted from the light combiner LC, and enters the speckle reduction device 140.

As is understood from the explanation described above, the laser light L1 is blue laser light having a center wavelength of 445 nm, the laser light L2 is green laser light having a center wavelength of 532 nm, and the laser light L3 is red laser light having a center wavelength of 635 nm. For this reason, the laser light emitted from the light combiner LC is white laser light. White light, not limited to white laser light, serves as a suitable illumination light in observation using the endoscope system 10. In other words, the light quantities of the laser light sources LD1, LD2, and LD3 are adjusted by the light source controller 130 so that the light emitted from the light combiner LC is substantially white light.

The speckle reduction device 140 that white laser light emitted from the light combiner LC enters includes a speckle reduction member 150 disposed to cross the optical path of the light emitted from the light source 120, and a driver 180 configured to drive the speckle reduction member 150.

The speckle reduction member 150 is formed of a member reducing coherent property, that is, coherence serving as the cause of generation of speckles. For example, the speckle reduction member 150 is formed of an optically transparent member having thickness variation. The details of the structure of the speckle reduction member 150 will be described later.

Movement of the speckle reduction member 150 may be, but not limited to, rotation movement, for example. For this reason, the speckle reduction member 150 has a rotation shaft 170. The driver 180 is configured to support the speckle reduction member 150 rotatably around the rotation shaft 170 and enable the speckle reduction member 150 to rotate around the rotation shaft 170.

The white laser light emitted from the light combiner LC passes through the speckle reduction device 140, thereby changes to a state in which coherence serving as the cause of generation of speckles is reduced, and thereafter enters the light condensing lens 190.

The light condensing lens 190 condenses the entering white laser light in order to cause the entering white laser light to enter the light guide 52 with high efficiency. The white laser light condensed by the light condensing lens 190 enters the light guide 52.

The light guide 52 guides the entering white laser light to the light emission unit 54 with high efficiency. The white laser light guided by the light guide 52 enters the light emission unit 54.

The light emission unit 54 emits the entering white laser light forward from the distal end of the endoscope 20. The light emitted from the endoscope 20 is applied to, for example, the observation target OT. The light applied to the observation target OT is, for example, reflected and/or scattered by the observation target OT.

Part of the light reflected or scattered by the observation target OT enters the imager 60 installed in the insertion distal end section 24*a* of the endoscope 20.

The imager 60 acquires an optical image of the observation target OT based on the entering light (reflected light or scattered light) from the observation target OT, and transmits an image signal thereof to the image processing circuit 220. The imager 60 is formed of, for example, a photoelectric transducer converting the received light into an electrical signal and outputting the electrical signal.

The imager 60 generates a plurality of temporally continuous still images, that is, moving images by repeatedly performing an imaging operation (including a light receiving operation and a read/transmission operation of the electrical signal). The unit period in time when the imager 60 repeatedly performs the imaging operation described above is referred to as "one imaging frame period".

By contrast, the laser light sources LD1 to LD3 are controlled by the light source controller 130 so as to have a width in laser light application time in one imaging frame period so that the white laser light of a light quantity suitable for observation is applied to the observation target OT even when the reflection and scattering intensity characteristics of the observation target OT changes.

In addition, each of the laser light sources LD1 to LD3 emits laser light of a light quantity necessary as accumulated light quantity while repeating flashing in one imaging frame period, in order to achieve the application light quantity suitable for observation of the observation target OT.

In the following explanation, the total time in which the laser light sources LD1 to LD3 apply laser light in one imaging frame period is referred to as an "application time in one imaging frame period".

In addition, the average of the application times in one imaging frame period in which the laser light sources LD1 to LD3 can emit light in the device system is referred to as an "average application time in one imaging frame period".

In addition, the application time in one imaging frame period that is shortest in application time in which the laser light sources LD1 to LD3 can emit light in the device system is referred to as a "shortest application time in one imaging frame period".

The image processing circuit 220 converts the image signal received from the imager 60 through, for example, the imaging cable into a signal proper for being displayed on the monitor 40, and transmits the signal to the monitor 40.

The monitor 40 displays the image of the observation target OT converted by the image processing circuit 220. The monitor 40 is formed of, for example, a liquid crystal display.

The light source controller 130 adjusts the emission light quantities of the laser light sources LD1, LD2, and LD3 by acquiring and analyzing the image signal from the image processing circuit 220 so that the image of the observation target OT is displayed with proper brightness on the monitor 40.

[Explanation of Speckles]

Speckles on the observation image are reduced by applying many speckle patterns in one imaging frame period. To achieve the reduction, it is important to sufficiently disperse the phases of laser light mutually matching in plane or temporally.

To apply various speckle patterns by sufficiently disperse the phases thereof, it is desirable that light of various phases are mixed in plane or temporally in the phases for one wavelength. For this reason, the speckle reduction member 150 is required to have a function of generating an optical path difference that shifts the phases of the entering light in plane or temporally continuously by a width for the wavelength.

That optical path difference is referred to as a "speckle reduction valid optical path difference" as an optical path difference valid for the speckle reduction member 150.

To reduce speckles in the image by applying various speckle patterns, it is desirable that the speckle reduction valid optical path difference generates an optical path difference for a specific wavelength in the applied light, from the viewpoint of dispersing the phases of the light. In particular, it is important to generate an optical path difference for the length of the longest wavelength. This is because generating the optical path difference for the longest wavelength enables generation of an optical path difference equal to or larger than the wavelength for light of a wavelength shorter than the longest wavelength. However, the structure is not limited thereto. When coherence of laser light of the longest wavelength is low enough to hardly cause appearance of speckles, it is unnecessary to generate an optical path difference for the length of the longest wavelength in the same manner. By contrast, when laser light greatly contributing to appearance of speckles is light other than the light of the longest wavelength, there are cases where an optical path difference for the wavelength should be actively provided. Accordingly, it is important to at least generate an optical path difference equal to or larger than the length of a specific wavelength in laser light emitted from the light source 120.

In addition, also for light with low coherence, it is unnecessary to generate an optical path difference for the length of the wavelength. The speckle reduction valid optical path difference in the case where speckles should be reduced produces an sufficient effect by generating at least an optical path difference of 1/10 or more as large as the wavelength in plane or temporally continuously.

The coefficient of 1/10 to 1 as large as the wavelength is referred to as "speckle reduction valid optical path difference magnification J".

In a light transmission valid region, the speckle reduction member 150 is formed of a member having a refractive index different from that of the air, and has thickness variation. In this manner, when light passes through the speckle reduction member 150, the optical distance with which the light has passed differs in the whole exit region. For this reason, the light emitted from the speckle reduction member 150 is caused to have more phases mutually different.

When $n_1$ is a refractive index of the speckle reduction member 150 existing on the light transmission valid region and $n_0$ is a refractive index of surrounding air, an optical path difference expressed by the following expression (1) can be generated.

$$(n_1 - n_0) \times h \tag{1}$$

Accordingly, it suffices that the thickness variation h expressed by the following expression (2) falls within the light transmission valid range.

$$h \geq J \times \lambda_{long}/(n_1 - n_0) \tag{2}$$

In the expression, $\lambda_{long}$ means the longest wavelength, and indicates the longest wavelength in the wavelengths included in the light emitted from the light source 120.

When the speckle reduction valid optical path difference magnification J is 1, the thickness variation h is expressed by the following expression (2-1).

$$h \geq \lambda_{long}/(n_1-n_0) \quad (2\text{-}1)$$

When the speckle reduction valid optical path difference magnification J is 1/10, the thickness variation h is expressed by the following expression (2-2).

$$h \geq 1/10 \times \lambda_{long}/(n_1-n_0) \quad (2\text{-}2)$$

As described above, the light applied to the observation target OT in the present embodiment is white laser light generated by combining blue laser light having a center wavelength of 445 nm, green laser light having a center wavelength of 532 nm, and red laser light having a center wavelength of 635 nm. Accordingly, the longest wavelength $\lambda_{long}$ is 635 nm.

The longest wavelength $\lambda_{long}$ is set to the center wavelength of the laser light source LD3 configured to emit light of the longest wavelength in the laser light sources LD1, LD2, and LD3 included in the light source 120.

When the speckle reduction valid optical path difference magnification J is 1/10, the refractive index $n_1$ of the speckle reduction member 150 is 1.5, and $n_0$ is 1.0, the difference in level of 123 nm or more serving as a value 1/5 as large as $\lambda_{long}$ is sufficient for generation of the optical path difference of the colors.

When the speckle reduction valid optical path difference magnification J is 1/10 and high-refractive-index glass "TAFD65" (nd=2.1) manufactured by HOYA Corporation is used as the speckle reduction member 150, the difference in level of 58 nm or more serving as a value of 1/11 as large as $\lambda_{long}$ is sufficient for generation of the optical path difference of the colors.

When the speckle reduction valid optical path difference magnification J is 1 and the refractive index $n_1$ of the speckle reduction member 150 is 1.5, thickness variation of 1265 nm serving as a value twice as large as $\lambda_{long}$ is sufficient for generation of the optical path difference of the colors.

Since it is used for illumination, the longest wavelength may be 700 nm serving as the longest wavelength in visible light. When the speckle reduction valid optical path difference magnification J is 1 and the refractive index $n_1$ of the speckle reduction member 150 is 1.5, the speckle reduction member 150 having thickness variation of 1400 nm (=1.4 μm) serving as a value twice as large as $\lambda_{long}$ is sufficient for generation of the optical path difference of the colors.

When the speckle reduction valid optical path difference magnification J is 1 and the refractive index $n_1$ of the speckle reduction member 150 is 2.1, difference in level of 577 nm serving as a value 0.9 times as large as $\lambda_{long}$ is sufficient for generation of the optical path difference of the colors.

The speckle reduction valid optical path difference magnification J can be properly determined in accordance with coherence of the light source 120 and the like.

[Shape of Difference in Level]

FIG. 4 illustrates the speckle reduction member 150 according to an example. As illustrated in FIG. 4, the speckle reduction member 150 has projections and depressions, that is, depression portions 152 and projection portions 154, on one of two surfaces, that is, the front surface and the back surface, through which light emitted from the light source 120 passes, for example, on an entrance surface 150a that light emitted from the light source 120 enters. Although the projections and depressions are not strictly divided into the depression portions 152 and the projection portions 154, the projections and depressions are schematically illustrated as the depression portions 152 and the projection portions 154 in FIG. 4. The thickness variation h is defined by a difference between the maximum thickness $T_{max}$ and the minimum thickness $T_{min}$ of the speckle reduction member 150.

As described above, since the speckle reduction member 150 should be provided with the function of generating the optical path difference that continuously shifts the phases of the entering light in plane, it is desirable that the thickness changes in multistages, or the thickness changes seamlessly (continuously) at least in portions other than the vertexes and the bottom points, as thickness variation. FIG. 5A to FIG. 5E illustrate some examples of cross-sectional shapes of thickness variation.

The thickness variation illustrated in FIG. 5A has projections and depression having difference in level of a rectangular shape of only one type. Specifically, the difference in height of the projections and depressions is only one type, and upper surfaces and bottom surfaces of the projections and depressions are completely plane surfaces. Such thickness variation can generate substantially only two types of speckle patterns generated in illumination time in one imaging period, and does not achieve effective speckle reduction.

The thickness variation illustrated in FIG. 5B includes projections and depressions having difference in level of rectangular shapes of a plurality of types. Specifically, although the upper surfaces and the bottom surfaces of the projections and depressions are completely plane surfaces, a plurality of types of differences in height of projections and depressions exist. By increase in type of differences, such thickness variation can generate more speckle patterns than those of the thickness variation illustrated in FIG. 5A, and has some effect of speckle reduction.

Figure 5C:
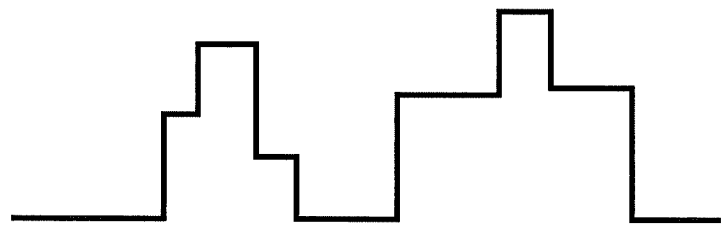
FIG. 5C illustrates a cross-sectional shape of thickness variation having projections and depressions having multi-stage differences in level of a plurality of types.

The thickness variation illustrated in FIG. 5C includes projections and depressions having multistage (step-like) differences in level of a plurality of types. Specifically, although the upper surface, the bottom surfaces, and the middle surfaces (step surface) of the projections and depressions are completely plane surfaces, a plurality of types of differences in height of the projections and depressions exist. By increase in type of differences, such thickness variation can generate further more speckle patterns than those of the thickness variations illustrated in FIG. 5A and FIG. 5B, and has more effect of speckle reduction.

Figure 5D:
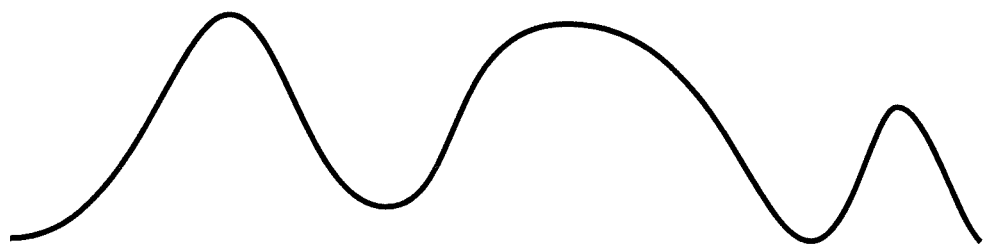
FIG. 5D illustrates a cross-sectional shape of thickness variation in which the thickness changes continuously and smoothly.

The thickness variation illustrated in FIG. 5D has a more effective shape than those of the thickness variations illustrated in FIG. 5A to FIG. 5C, and has a thickness changing continuously and smoothly. Various member thicknesses exist also between the vertexes and the bottom surfaces. For this reason, light passing through the point is emitted through various optical path differences. This structure innumerably increases speckle patterns that can be generated, and is more effective for speckle reduction.

In more detail, in the case of the shape illustrated in FIG. 5D, since flat portions exist in the lateral direction on the paper between close points around the vertex and between close points around the bottom point, it cannot be said definitely that the shape can sufficiently form the optical path difference.

Figure 5E:
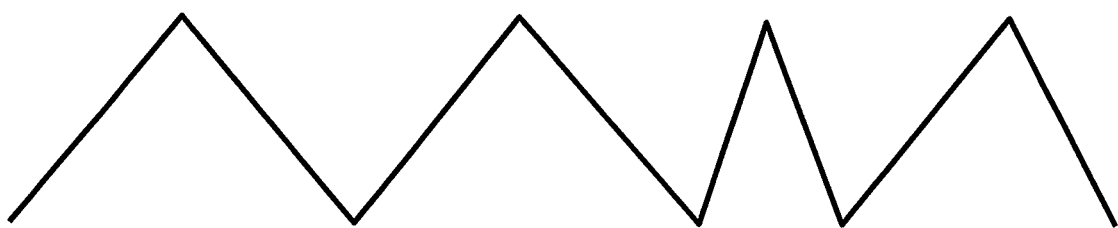
FIG. 5E illustrates a cross-sectional shape of thickness variation having a shape generating an optical path difference also at vertexes and therearound and bottom points and therearound.

The thickness variation illustrated in FIG. 5E has a most efficient shape in the thickness variations illustrated in FIG. 5A to FIG. 5E, and has a shape generating an optical path difference also at vertexes and thereabout and bottom points and thereabout and more effective.

Specifically, the thickness variation preferably has a (multistage or continuous) shape having at least one point having an optical path length different from a relevant maximum thickness point and a relevant minimum thickness point all between closest maximum and minimum points.

The maximum thickness point and the minimum thickness point are points having local maximum value and minimum value in thickness variation. The between closest maximum and minimum points means between all the maximum thickness point and the minimum thickness point respectively closest to the maximum thickness points existing in the light transmission valid region, on a plane perpendicular to the optical axis, when the speckle reduction member 150 is viewed in a direction parallel to the optical axis.

As illustrated in FIG. 6, the speckle reduction member 150 more preferably has projections and depressions, that is, depression portions 152 and projection portions 154 on both of two surfaces, that is, the front surface and the back surface, through which light emitted from the light source 120 passes, for example, on both of the entrance surface 150a that light emitted from the light source 120 enters and the exit surface 150b that the light that has entered the speckle reduction member 150 exits. Also in FIG. 6, the projections and depressions are specifically illustrated as depression portions 152 and projection portions 154.

When a sufficient optical path difference is to be generated only with one surface, the difference in level of projections and depressions increases, and scattering in the surface increases. By contrast, forming projections and depressions in both surfaces removes the necessity for increasing the difference in level of each of projections and depressions. This structure enables reduction in scattering degree of the whole speckle reduction member 150, and enables light to enter the light guide 52 with high efficiency.

The average intervals between the projections and depressions are desirably larger than the wavelength. When the intervals between the projections and depressions are about equal to the wavelength, light that have been transmitted through adjacent projecting portions interferes with each other, and are strongly emitted in a direction inclined with respect to the optical axis. This structure deteriorates the entrance efficiency into the light guide 52 disposed ahead.

As illustrated in FIG. 7, when the speckle reduction member 150 is viewed in a direction parallel to the optical axis, supposing that a straight-line difference (a distance on a plane perpendicular to the optical axis) to the closest maximum thickness point for any "maximum thickness point" (a point having the local maximum value in thickness variation) in the light transmission valid region is a "distance between close maximum thickness points" d, the average of all distances d between close maximum thickness points is desirably at least larger than $5 \times \lambda_{long}$.

By forming the projections and depression with intervals of such a degree of distance therebetween as an average, interference therebetween can be effectively reduced, and the entrance efficiency into the light guide 52 disposed ahead is not decreased.

[Entrance Efficiency]

As described above, the light guide 52 may be formed of a single-line optical fiber, or a bundle fiber obtained by bundling a plurality of optical fibers.

By causing light to enter the core portion of the optical fiber at a predetermined angle, the optical fiber can guide the light with high efficiency. Accordingly, the valid entrance region in the light guide 52 is an entrance end surface of the core portion.

By contrast, in a bundle fiber, optical fibers are generally bundled in a circular shape in accordance with the light condensing region shape for the entering light. Accordingly, a valid entrance region of a bundle fiber is a region obtained by connecting, in a circular shape, the outside portions of the core portions of optical fibers located outermost in optical fibers bundled in a circular shape. A valid entrance region of a bundle fiber that is not bundled in a circular shape is a region obtained by connecting, in a straight-line shape, outside portions of the core portion of optical fibers located outermost.

When the projections and depressions of the speckle reduction member 150 have a large inclination angle, in addition to the function of continuously generating a number of optical path differences, the speckle reduction member 150 is provided with a function of scattering light.

When white laser light that has been transmitted through the speckle reduction member 150 is scattered, the light condensing effect into the light guide 52 by the following light condensing lens 190 decreases, and the light quantity going off the valid entrance region of the light guide 52 increases.

The expression "valid entrance region of the light guide 52" means a region disposed in the entrance surface of the light guide 52 and capable of effectively guiding the entering light. In the following explanation, the valid entrance region of the light guide 52 is also referred to as a "light guide valid entrance region".

When the light quantity going off the valid entrance region of the light guide 52 increases, the entering light quantity reduces, and light from the light source 120 cannot be effectively used for illumination.

Accordingly, the average inclination angle of the projections and depressions of the speckle reduction member 150 should set to a predetermined angle or less while maintaining the speckle reduction effect.

The following is consideration on the predetermined inclination angle of the projections and depressions.

Figure 8:
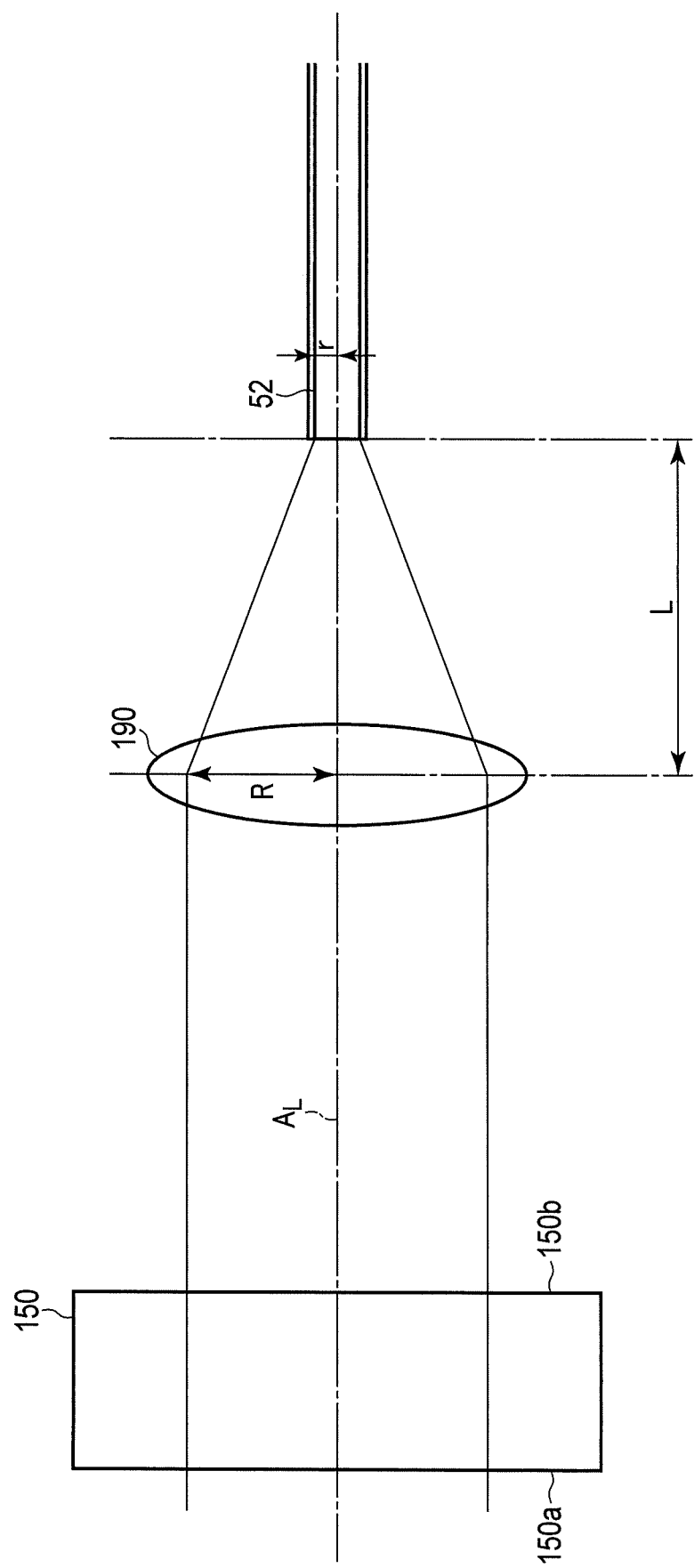
FIG. 8 illustrates geometrical-optical relation among a speckle reduction member having an entrance surface and an exit surface perpendicular to the optical axis, a light condensing lens, and a light guide.

If no speckle reduction member 150 exists, or if both the entrance surface 150a and the exit surface 150b are completely perpendicular to the optical axis $A_L$ and planes, although the speckle reduction member 150 exists as illustrated in FIG. 8, optical design is performed so that light substantially uniformly enters the valid entrance region of the light guide 52.

Figure 10:
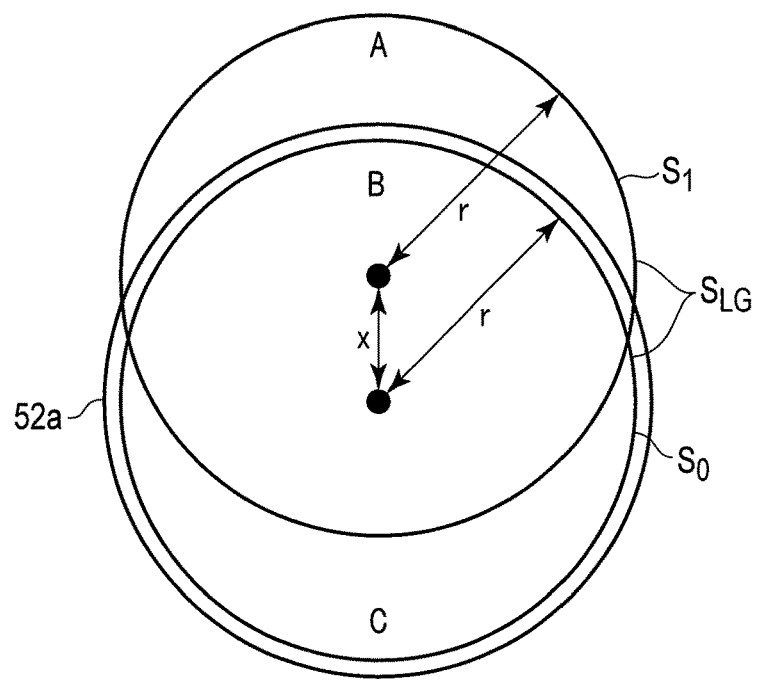
FIG. 10 illustrates a light guide valid entrance region, a perpendicular plane application region, and an inclined plane application region.

For the white laser light that is condensed by the light condensing lens 190 and then reaches the light guide 52, as illustrated in FIG. 10, when the shape projected onto the surface including the entrance surface of the light guide 52 is defined as a "light guide application region" $S_{LG}$, the light guide application region $S_{LG}$ and the light guide valid entrance region 52a are designed that so as to be substantially coincident with each other, or so that the light guide application region $S_{LG}$ is smaller than the light guide valid entrance region 52a. Here, supposing that, in the in-plane application intensity distribution of the light applied to the entrance surface of the light guide 52, the light guide application region $S_{LG}$ is a region irradiated with an intensity larger than $1/e^2$ in comparison with the maximum intensity.

By contrast, by considering the case where only the exit surface of the speckle reduction member 150 is "uniformly" inclined, the "predetermined angle" with respect to the average inclination angle of the projections and depressions of the speckle reduction member 150 is calculated.

Figure 9:
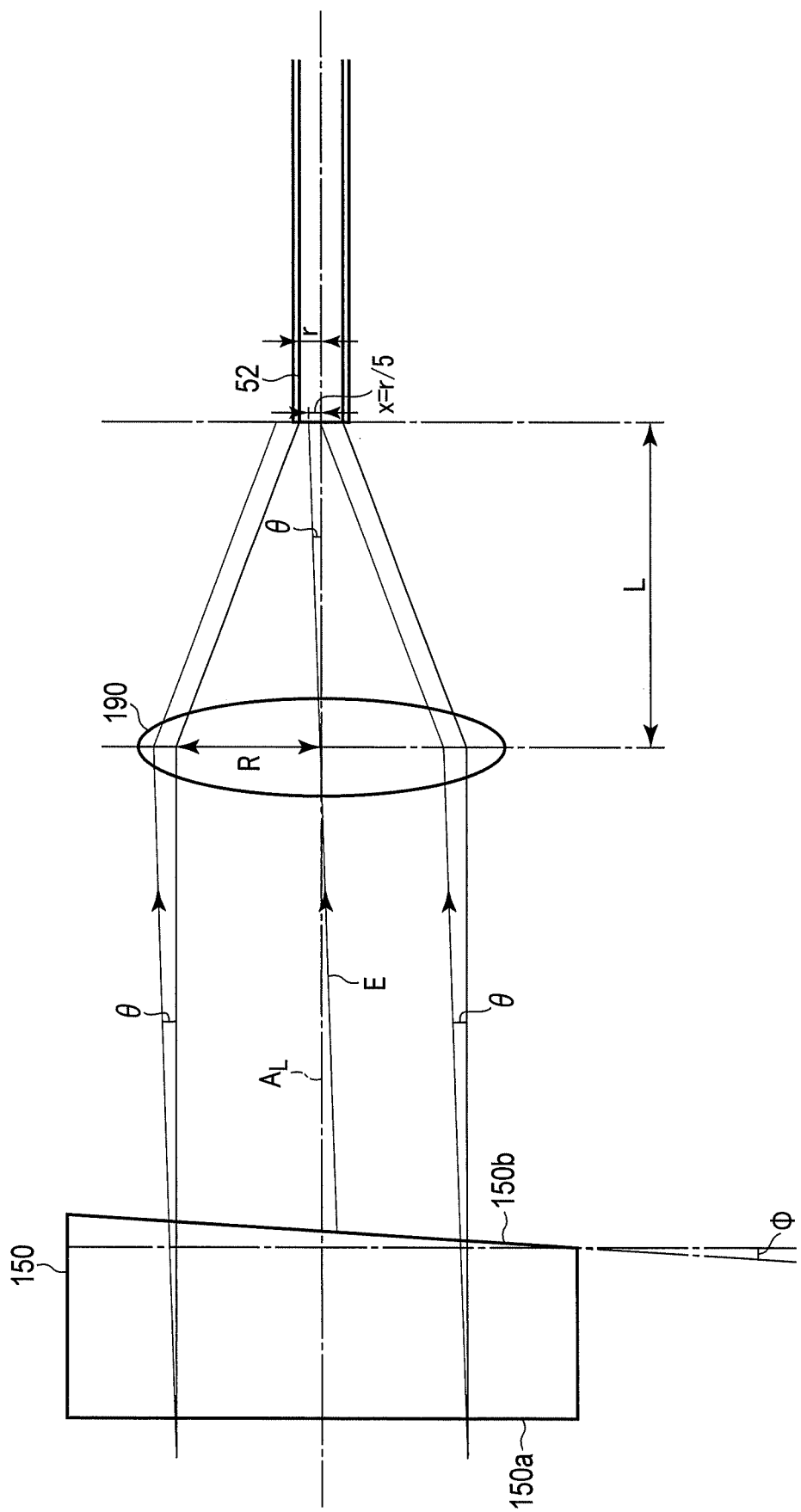
FIG. 9 illustrates geometrical optical relation among a speckle reduction member having an entrance surface perpendicular to the optical axis and an exit surface inclined with respect to the optical axis, the light condensing lens, and the light guide.

As illustrated in FIG. 9, suppose that the entrance surface 150a of the speckle reduction member is set perpendicularly to the optical axis $A_L$, while the exit surface 150b uniformly has an inclination with an inclination angle $\Phi$ with respect to the plane perpendicular to the optical axis $A_L$.

In this case, since parallel light enters the exit surface 150b of the speckle reduction member 150 from the rear (from the side of the entrance surface 150a), the light is uniformly emitted with an angle θ in accordance with Snell's law.

In the light flux, a ray E that has passed through the center of the light condensing lens 190 is hardly curved by the light condensing lens 190 and goes toward the light guide 52.

The ray E applied to the entrance surface of the light guide 52 enters a point shifted with a shift width x from the center of the light guide valid entrance region 52a, as illustrated in FIG. 10, in comparison with the case (FIG. 8) where no speckle reduction member 150 exists. The point serves as the center of the application region $S_{LG}$.

When it is considered to which extent the shift width x is allowable as the endoscope illumination, it is considered as valid to allow a shift up to 10% with respect to the longest width of the light guide valid entrance region 52a (=effective allowable shift rate).

When the region is shifted by 10% with respect to the longest width of the light guide valid entrance region 52a, the ratio (A/(A+B) or C/(B+C) in FIG. 10) of the portion of the inclined plane application region $S_1$ that does not overlap the perpendicular plane application region $S_0$ to the size of the perpendicular plane application region $S_0$ is limited to approximately 13% (see the following calculation expression) in calculation. In this example, suppose that an antireflection film or the like is provided on both of the entrance surface 150a and the exit surface 150b of the speckle reduction member 150, and reflection loss caused by the difference in refractive index for the entering light to the speckle reduction member 150 does not substantially exists.

The perpendicular plane application region $S_0$ means the application region $S_{LG}$ of the light that has passed the speckle reduction member 150 having the entrance surface 150a and the exit surface 150b perpendicular to the optical axis $A_L$, as illustrated in FIG. 8. In addition, the inclined plane application region $S_1$ means the application region $S_{LG}$ of the light that has passed the speckle reduction member 150 having the entrance surface 150a perpendicular to the optical axis $A_L$ and the exit surface 150b inclined with respect to the optical axis $A_L$, as illustrated in FIG. 9.

Accordingly, even when the light guide valid entrance region 52a has the same shape as the perpendicular plane application region $S_0$ of the speckle reduction member 150 and the light quantity distribution in the application region S is uniform, the loss is limited to the light quantity loss of approximately 13%. For this reason, it is possible to enjoy the speckle reduction effect achieved by the present invention without greatly changing the device structure.

Accordingly, with respect to the speckle reduction member 150, when the entering light quantity when the speckle reduction member 150 exists is 13% or less with respect to the entering light quantity into the light guide 52 when no optical path difference exists in the speckle reduction member 150, the loss rate of the entering light quantity is equal to or smaller than an "effective allowable loss rate".

The effective allowable loss rate is a loss rate with which the speckle reduction effect by the present invention can be enjoyed by, for example, simply setting the speckle reduction member 150 on the optical path without greatly changing the structure of the device. As a specific definition, the effective allowable loss rate means a loss rate with which a difference between the entering light quantity (entering light quantity without optical path difference) into the light guide 52 when the speckle reduction member 150 with no optical path difference in plane is set and the entering light quantity when the speckle reduction member 150 with the speckle reduction valid optical path difference is set is equal to or smaller than the predetermined rate of the entering light quantity without optical path difference. In this example, the predetermined rate is set to 13% for the reason described above.

The explanation described above illustrates an ordinary effective allowable shift rate, but the structure is not limited thereto. For example, in an endoscope device suitable for observation close to the observation target OT, the small light quantity does not cause much problem. Conversely, since the image is easily blurred due to movement of the observation target OT, a short exposure time is required. In such an endoscope device, the effective allowable shift rate may be large, and sufficient speckle reduction is required. In such a case, there are cases where the effective valid shift rate of 50% is allowed.

Conversely, in an endoscope device mainly performing observation of a distant view, a large light quantity is required. In such an endoscope device, a small effective allowable shift rate or effective allowable loss rate is required. For example, there are cases where only a shift rate less than 5% is allowed.

The following is an explanation of calculation of the rate of the portion of the application region $S_1$ that does not overlap the perpendicular plane application region $S_0$ to the size of the perpendicular plane application region $S_0$, when the region is shifted by 10% with respect to the longest width of the light guide valid entrance region 52a.

In FIG. 10, the total area $S_{A+B}$ of the "region A+region B" is expressed by the following expression (3), and the area $S_A$ of the region A is expressed by the following expression (4).

$$S_{A+B} = \pi \times r^2 \quad (3)$$

$$S_A = 2 \times (\pi \times r^2 \times (\arccos(-1/10))/2\pi + 99^{1/2}/100 \times r^2 - \pi \times r^2 \times (\arccos(1/10))/2\pi \quad (4)$$

Suppose that 2r is the longest width of the light guide valid entrance region 52a. In the case where the light guide valid entrance region 52a has a circular shape, the radius is r. L is a distance on the optical axis from the center of the light condensing lens 190 to the light guide valid entrance region 52a.

When the shift width x is 10% as large as the longest width of the light guide valid entrance region 52a, that is, r/5, the exit inclination angle θ is expressed by the following expression (5) from FIG. 9.

$$\theta = \arctan(x/L) = \arctan(r/5L) \quad (5)$$

Figure 11:
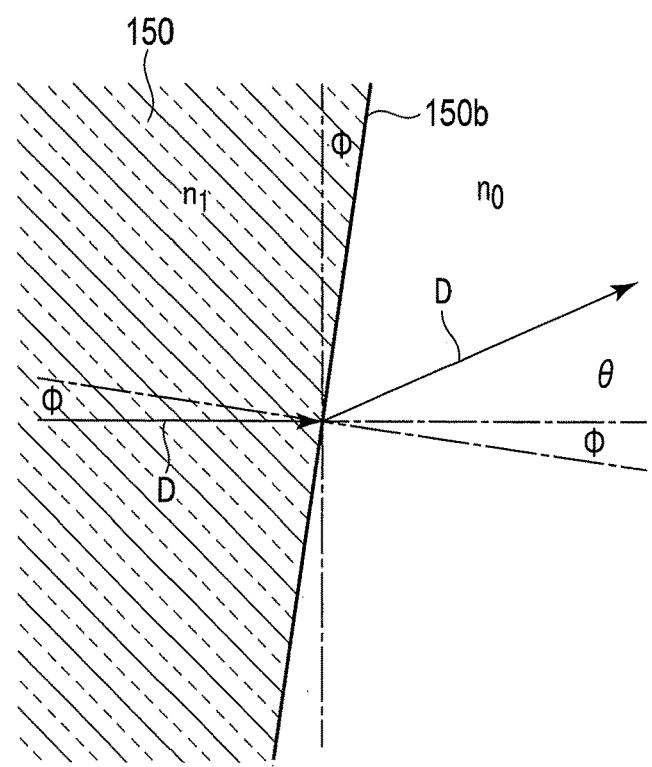
FIG. 11 illustrates relation between an inclination angle of the exit surface of the speckle reduction member and an exit inclination angle.

With reference to FIG. 11, the inclination angle θ of the exit surface 150b of the speckle reduction member 150 with which the exit inclination angle is θ is calculated. It suffices that the ray D emitted in accordance with Snell's law has an inclination θ calculated as described above from the optical axis $A_L$.

Accordingly, the following expression (6) is acquired by Snell's law.

$$n_1 \sin \Phi = n_0 \sin(\Phi + \theta)$$

$$n_1 \sin \Phi = n_0(\sin \Phi \cos \theta + \cos \Phi \sin \theta)$$

$$\sin \Phi (n_1 - n_0 \cos \theta) = \cos \Phi (n_0 \sin \theta)$$

$$\tan \Phi = n_0 \sin \theta / (n_1 - n_0 \cos \theta) \quad (6)$$

Accordingly, the inclination angle $\Phi$ of the speckle reduction member 150 is calculated by the following expression (7).

$$\Phi = \arctan(n_0 \sin \theta / (n_1 - n_0 \cos \theta)) \tag{7}$$

When the expression (5) is substituted into the expression (7), the following expression (8) is acquired.

$$\Phi = \arctan(n_0 \sin(\arctan(r/5L)) / (n_1 - n_0 \cos(\arctan(r/5L)))) \tag{8}$$

Generally, the radius r of the light guide valid entrance region 52a is designed to be ⅕ or less as large as the lens valid radius R of the light condensing lens 190, in consideration of the chromatic aberration.

By contrast, the light condensing distance L is designed to be twice or more as large as the lens valid radius R, also in consideration of aberration.

Specifically, generally, it is designed to satisfy "r/L=1/10 or less". In consideration of it (r/L≤1/10), the inclination angle is approximately 2° or less.

In view of the above, when the speckle reduction member 150 uniformly has inclination of only the inclination angle, the angle achieving that the center of gravity, for example, the center, of the light guide application region $S_{LG}$ of light that is transmitted through the speckle reduction member 150 and applied to a plane including the light guide valid entrance region 52a has a shift quantity of 1/10 or less in comparison with the diameter of the light guide valid entrance region 52a with respect to the center of gravity, that is, the center, of the application region $S_{LG}$ of light that is applied to the plane including the light guide valid entrance region 52a when no speckle reduction member 150 exists is 2° when r/L is 1/10, as described above.

Figure 12A:
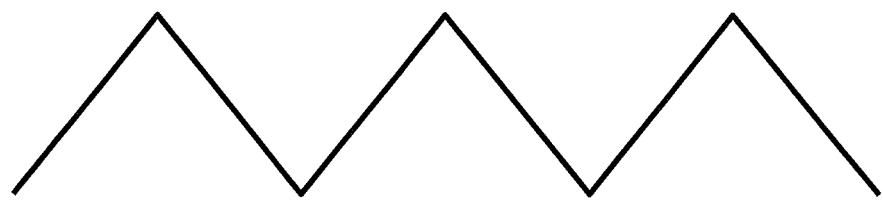
FIG. 12A illustrates the speckle reduction member having an exit surface formed of only conical inclined surfaces having a uniform inclination angle.

The light quantity loss is approximately 13% in the same manner, also when the exit surface in the light transmission valid region of the speckle reduction member 150 is a surface formed of only conical inclined surfaces having a uniform inclination angle $\Phi$ as illustrated in FIG. 12A.

Figure 12B:
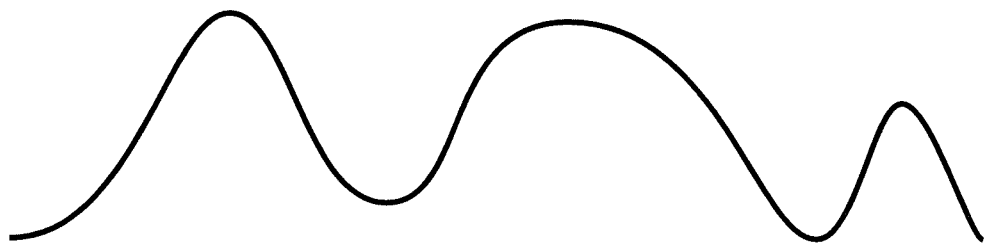
FIG. 12B illustrates the speckle reduction member having an exit surface formed of only conical inclined surfaces having an average inclination angle, although not uniform.

In addition, the light quantity loss is approximately 13% in the same manner, also when the exit surface in the light transmission valid region of the speckle reduction member 150 is a surface formed of only conical inclined surfaces having an average inclination angle $\Phi$, although not uniform, as illustrated in FIG. 12B.

Figure 13:
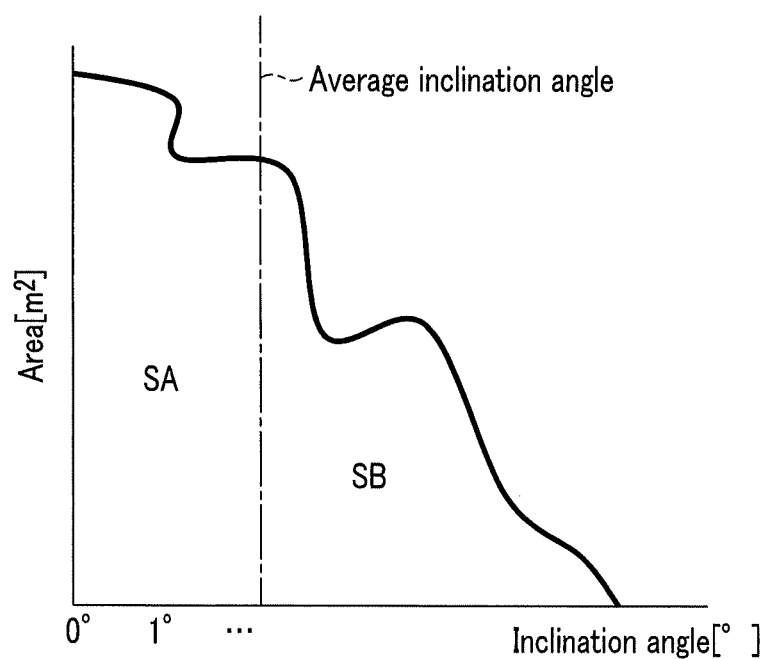
FIG. 13 is a graph illustrating the average inclination angle.

As illustrated in FIG. 13, the average inclination angle indicates an angle when the area is half of the whole area of the symmetrical regions (that is, when "SA=SB" is satisfied), when the areas are integrated in order from the inclination angle 0°, in a graph having a vertical axis being the total area of places having the same inclination angle (however, it has a minute angle range, and the azimuth angle (in which direction the angle is inclined) is not considered) in the symmetrical regions.

Accordingly, when the average inclination angle with the definition as described above is formed in the exit surface of the speckle reduction member 150, the light usage efficiency is substantially maintained, and the speckle reduction effect can be enjoyed.

The following is another definition of the inclination angle. It is referred to as "average inclination angle characteristic value" using a ratio of the arithmetic average roughness Ra defined by JIS to an average length RSm of the roughness curve element.

Figure 14:
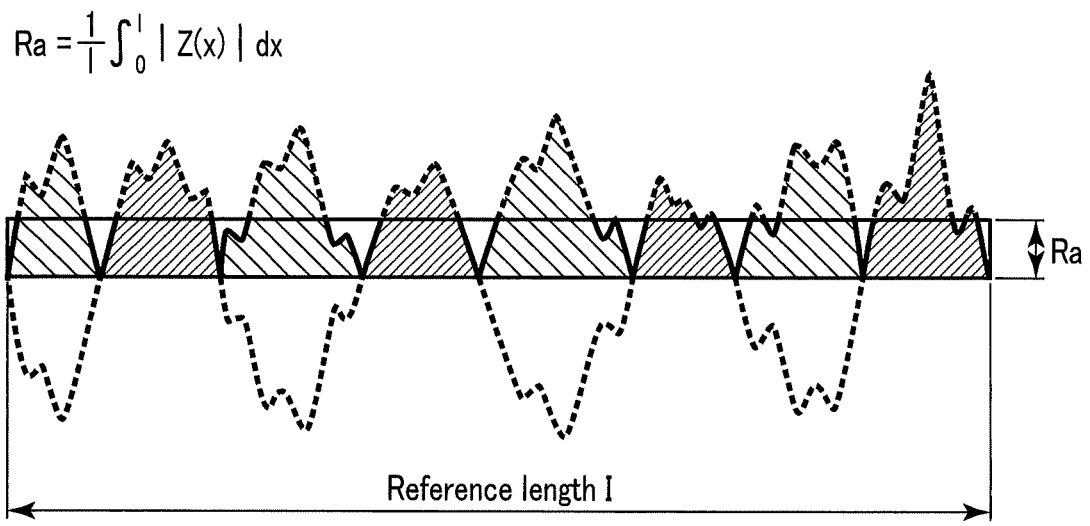
FIG. 14 is a diagram illustrating definition of arithmetic average roughness.

The arithmetic average roughness Ra is a parameter in the vertical direction, and defined with an average of the absolute values of height information Z(x) in the reference length I, as illustrated in the expression in FIG. 14. The height information Z(x) indicates height of the contour curve forming the surface from an average line.

Figure 15:
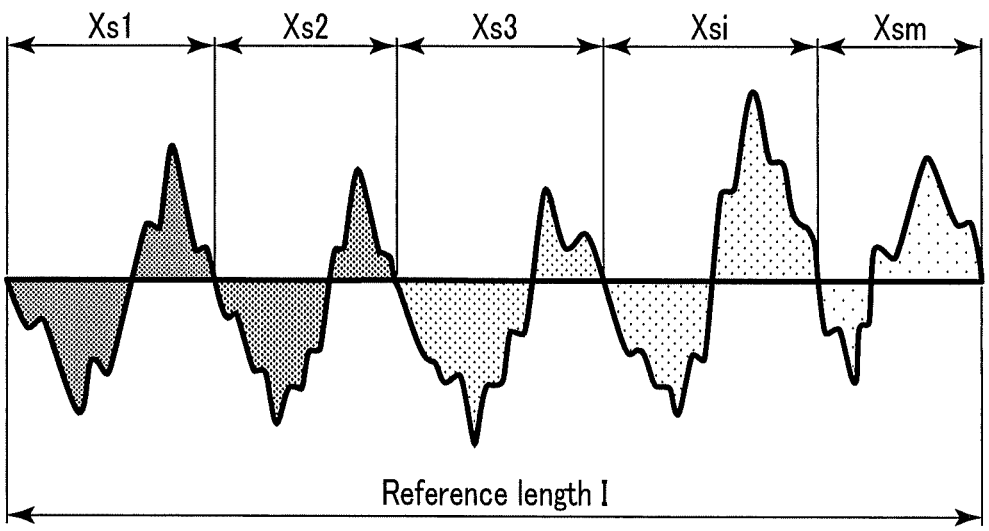
FIG. 15 is a diagram illustrating definition of average length of roughness curve elements.

The average length RSm of the roughness curve element is a parameter in a horizontal direction, and is defined by the average of lengths Xsi (i=1, ..., m) of the contour curve elements in the reference length I, as illustrated with the expression in FIG. 15.

4Ra/RSm is defined as the average inclination angle characteristic value. This serves as a parameter equal to the tangent of the average inclination angle in definition. For this reason, for example, when it is proper that the average inclination angle is 2° or less, it means that the average inclination angle characteristic value satisfying "4Ra/RSm≤0.040" is proper.

The value is referred to as a parameter "effective valid average inclination angle characteristic value", as an effective valid average inclination angle characteristic value.

In the case of using an endoscope suitable for close observation, since the effective valid shift rate described above up to 50% is allowed, "x=r/2" is satisfied, the effective valid average inclination angle is 5.7°, and the effective valid average inclination angle characteristic value is 0.100.

In addition, in the case of using a screening endoscope, since the effective valid shift rate is 5%, "x=r/10" is satisfied, the effective valid average inclination angle is 1.1°, and the effective valid average inclination angle characteristic value is 0.020.

The embodiment has illustrated the example in which inclination is formed in the exit surface of the speckle reduction member 150, but the structure is not limited thereto. When inclination is formed in the entrance surface, the average inclination angle is desirably roughly set to the angle range described above, although the light refraction phenomenon is slightly different.

[Rotation]

Speckle reduction by the speckle reduction member 150 produces more effect by performing dispersion temporally as well as in plane.

By moving the speckle reduction member 150 during application of laser light, the speckle reduction member 150 is enabled to temporarily change the phase of the light passing through the same point in the entrance surface of the speckle reduction member 150, and such a structure is more desirable.

The light source device 110 has the "average application time in one imaging frame period" as the average of "application times in one imaging frame period" in which the laser light sources LD1 to LD3 can emit light in the device system.

During the average application time in one imaging frame period, the speckle reduction member 150 is moved during the application time in directions substantially perpendicular to the optical axis in the whole area of the speckle reduction member application region, and thereby enabled to temporarily disperse the phase of the light.

In the structure, the expression "speckle reduction member application region" means a light application region for the speckle reduction member 150.

Specifically, as illustrated in FIG. 16, for all points P in the speckle reduction member application region $S_{SP}$, it is desirable that laser light to be transmitted through the speckle reduction member 150 is transmitted through the thickness variation of the speckle reduction member 150 by the quantity to at least generate the optical path difference of $1/10 \times \lambda_{long}$ or more during the "average total application time in one imaging frame period".

FIG. 16 schematically illustrates relative movement of the speckle reduction member application region $S_{SP}$ with respect to counterclockwise rotation of the speckle reduction member 150 illustrated with an arrow DR.

Since it is impossible to provide from which portion in the speckle reduction member 150 one imaging frame period starts, it is desirable that laser light to be transmitted through the speckle reduction member 150 is transmitted through the thickness variation of the speckle reduction member 150 by the quantity to at least generate the optical path difference of $1/10 \times \lambda_{long}$ or more, even when which portion in the speckle reduction member 150 the imaging frame period starts.

To achieve it, it is desirable to actively form thickness variation in the circumferential direction of the speckle reduction member 150.

Figure 17A:
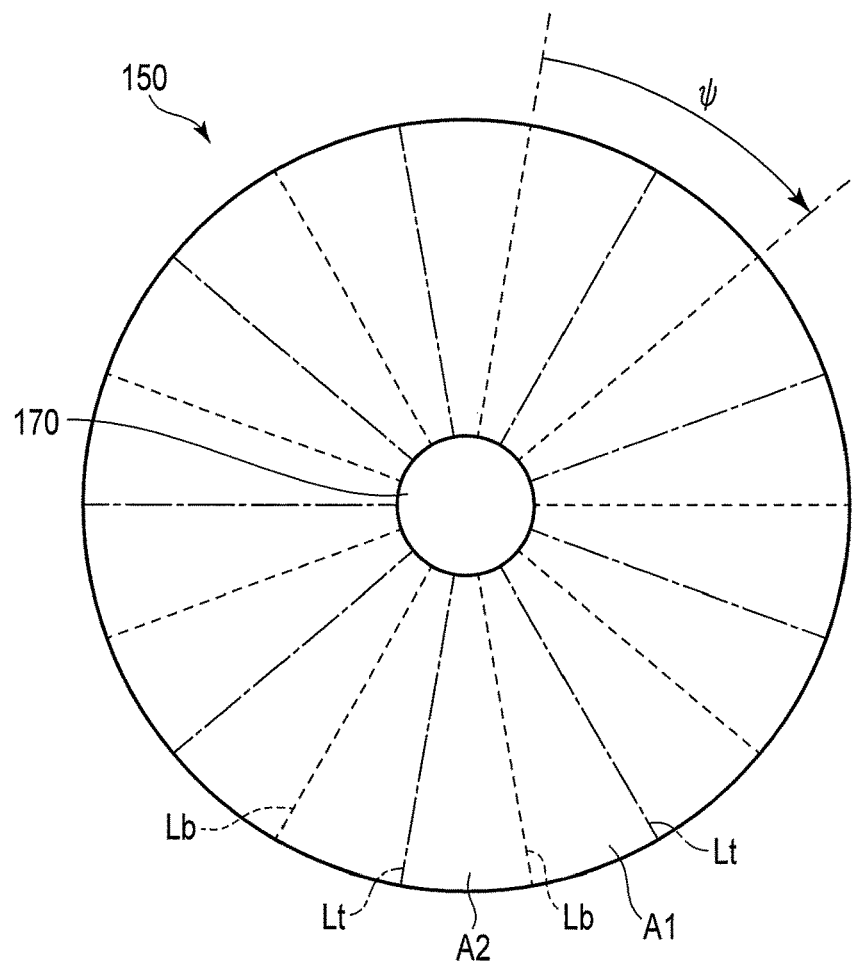
FIG. 17A is a plan view of the speckle reduction member having projections and depressions having difference in level in a fan-like manner.
Figure 17B:
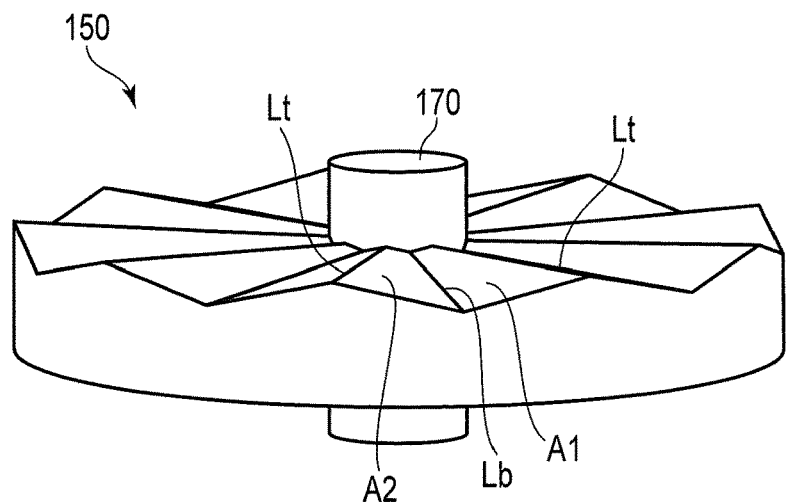
FIG. 17B is a perspective view of the speckle reduction member illustrated in FIG. 17A.

For example, as illustrated in FIG. 17A and FIG. 17B, the projections and depressions included in the speckle reduction member 150 desirably have a shape provided with fan-shaped inclined surfaces A1 and A2 so that the light passes through an optical path difference of $1/10 \times \lambda_{long}$ twice, that is, the ascent and descent, during the angle ψ with which the speckle reduction member 150 rotates in the average total application time in one imaging frame period.

The speckle reduction member 150 illustrated in FIG. 17A and FIG. 17B has projections and depressions formed by repeatedly arranging fan-shaped surfaces A1 descending from a top line Lt toward a bottom line Lb with a fixed inclination angle and fan-shaped inclined surfaces A2 ascending from a bottom line Lb toward a top line Lt with a fixed inclination angle in a circumferential direction.

With this structure, even when application in one frame period starts from any point in the speckle reduction member 150, the light can pass an optical path difference of $1/10 \times \lambda_{long}$ in all points in the speckle reduction member application region.

When the observation target OT has high reflection and scattering characteristics or the observation target OT is close, the illumination light quantity desirably achieves a dark state. For this reason, an imaging frame with application time shorter than the average total application time in one imaging frame period also exists in the device system.

In such a case, although the light cannot pass through a sufficient optical path difference, there are cases where the speckle reduction effect is not required much, for example, the image is a close image and difficult to achieve focusing and unify aberration in the whole image region.

In addition, it is desirable that at least an optical path difference of 1/10 or more as large as the longest wavelength exists in the whole desired shortest light transmission region through which the light passes in the "shortest application time in one imaging frame period" that is shortest in the time in which the illumination device emits light in one imaging frame period.

This structure achieves effective speckle reduction under all the observation conditions.

In addition, as illustrated in FIG. 18A and FIG. 18B, the speckle reduction member 150 may include random projections and depressions. The random projections and depressions are schematically illustrated as projection portions 158 having various sizes and arranged at random, in FIG. 18A and FIG. 18B. The speckle reduction member 150 having the random projections and depressions as described above can produce sufficient effect, as long as the laser light to be transmitted through the speckle reduction member 150 can pass through an optical path difference of $1/10 \times \lambda_{long}$ in all points of the speckle reduction member application region, within the shortest total application time in one imaging frame period.

In addition, when the rotation speed of the speckle reduction member 150 is designed to move by a distance larger than $5 \times \lambda_{long}$ with the shortest time in the total application time in one imaging frame period to apply light in one imaging frame period, in a point having the shortest moving distance with respect to the speckle reduction member application region, the speckle reduction member 150 can effectively reduce speckles, because light diffraction hardly occurs, and the phase of light can be sufficiently temporally dispersed.

Ordinary glasses have thickness variation of a wavelength substantially equal to visible light or around in both front and back surfaces as "warps" and/or "waviness", unless processed with high accuracy. However, since intervals on plane of the thickness variation are widely distributed, to use the glass as the speckle reduction member 150, it is required to increase the speed of rotation so that the speckle reduction member 150 can move by a distance between the closest maximum and minimum points in the shortest application time.

However, in a structure requiring a small speckle reduction effect, such as a structure in which speckles have originally been reduced, an ordinary glass may be introduced in a portion before the light guide 52 and used while being rotated, as a desirable example.

Glasses generally called "standard quality grade glasses" often have waviness having a height substantially equal to the visible light wavelength or around at intervals of 10 mm on average. In other words, standard quality grade glasses generally have average unevenness intervals of approximately 10 mm. For this reason, in the case of using a standard quality grade glass is used as the speckle reduction member 150, the speckle reduction member 150 is desirably moved by 10 mm or more during one imaging frame period in a point having the shortest moving distance.

Movement of the speckle reduction member 150 by the driver 180 is not limited to rotation movement. For example, as illustrated in FIG. 19A, the speckle reduction member 150 may be moved by the driver 180 to perform swing movement moving along an 8-shaped track T1. Alternatively, as illustrated in FIG. 19B, the speckle reduction member 150 may be moved by the driver 180 to perform shaking movement in which the speckle reduction member 150 reciprocats along a straight-line track T2.

By the speckle reduction device 140 having such a structure, the speckle reduction member 150 can be miniaturized. This structure achieves reduction in size of the speckle reduction device 140, and the light source device 110 by extension.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope light source device configured to emit light for illuminating an observation target through an endoscope to be connected thereto, comprising:
   a light source configured to emit light having a predetermined wavelength and coherence;

a speckle reduction member that is disposed to cross an optical path of the light emitted from the light source, that has a surface including thickness variation that provides the light with a speckle reduction valid optical path difference or more corresponding to the predetermined wavelength, and that is configured to scatter the entering light;

a driver configured to move the speckle reduction member; and a light condensing lens configured to condense the light that has passed through the speckle reduction member onto a light guide of the endoscope, the surface of the speckle reduction member including the thickness variation having inclination of a predetermined average inclination angle with respect to a plane perpendicular to an optical axis, and the predetermined average inclination angle being determined so that a light quantity loss rate of the entering light into the light guide by scattering of the speckle reduction member and refraction of the light condensing lens has a positive value equal to or smaller than an effective allowable loss rate.

2. The endoscope light source device according to claim 1, wherein
the light source is configured to emit the mutually different light beams, the endoscope light source device further comprising
a light combiner coaxially configured to combine the mutually different light.

3. The endoscope light source device according to claim 1, wherein
the light source is configured to emit light having wavelengths,
the speckle reduction member has a light transmission valid region through which the light is transmitted,
the speckle reduction valid optical path difference is a difference between a member thickness of a thinnest portion and a member thickness of a thickest portion existing in the light transmission valid region, and
the speckle reduction valid optical path difference is at least equal to or larger than a distance calculated by the following expression:

$$J \times \lambda_{long}/(n_1 - n_0)$$

where $n_1$ is a refractive index of the speckle reduction member existing on the light transmission valid region,
$n_0$ is a refractive index of surrounding air,
$J$ is a speckle reduction valid optical path difference magnification, and
$\lambda_{long}$ is a longest wavelength in the wavelengths included in the light.

4. The endoscope light source device according to claim 3, wherein
the thickness variation has a multistage or continuous shape having at least one point having an optical path length different from a relevant maximum thickness point and a relevant minimum thickness point all between closest maximum and minimum points.

5. The endoscope light source device according to claim 4, wherein
the speckle reduction member has projections and depressions in both of an entrance surface that the light enters and an exit surface that the light exits.

6. The endoscope light source device according to claim 4, wherein
the speckle reduction member has projections and depressions on an entrance surface that the light is enters or an exit surface that the light exits or both in the light transmission valid region, and
the thickness variation is at least 1.4 μm or more.

7. The endoscope light source device according to claim 5, wherein
an average of all distances between close maximum thickness points in the light transmission valid region is larger than $5 \times \lambda_{long}$.

8. The endoscope light source device according to claim 5, wherein
the endoscope includes a light guide configured to guide the light emitted from the endoscope light source device,
the light guide includes an entrance surface that the light emitted from the endoscope light source device enters, and a light guide valid entrance region on the entrance surface of the light guide, the light guide valid entrance region being a region capable of effectively guiding the entering light,
when the entrance surface of the speckle reduction member is perpendicular to the optical axis, and the exit surface of the speckle reduction member uniformly has inclination of only the average inclination angle,
the predetermined average inclination angle of the projections and depressions of the speckle reduction member is equal to or smaller than an angle achieving that a shift quantity between the center of gravity of a light guide application region of light that is transmitted through the speckle reduction member and applied to a plane including a light guide entrance region and the center of gravity of a light guide application region of light that is applied to the surface including the light guide entrance region when no speckle reduction member exists is a ratio of the effective allowable shift rate in comparison with the longest width of the light guide valid entrance region.

9. The endoscope light source device according to claim 8, further comprising:
a light condensing lens disposed between the speckle reduction member and the light guide, wherein
the predetermined average inclination angle Φ is expressed by the following expression:

$$\Phi \le \arctan(n_0 \times \sin(\arctan(r/5L))/(n_1 - n_0 \times \cos(\arctan(r/5L)))),$$

where $2r$ is the longest width of the light guide valid entrance region, and L is a distance from the light condensing lens to the light guide valid entrance region.

10. The endoscope light source device according to claim 9, wherein
an average inclination angle characteristic value 4Ra/RSm for the projections and depressions of the speckle reduction member is equal to or smaller than an effective valid average inclination characteristic value.

11. The endoscope light source device according to claim 3, wherein
the endoscope includes an imager configured to image the observation target and, when a unit period in time when the imager repeatedly performs an imaging operation is one imaging frame period,
the speckle reduction member is moved by the driver so that the light to be transmitted through the speckle reduction member is transmitted through the thickness variation by a quantity to at least generate the speckle reduction valid optical path difference corresponding to the longest wavelength in the wavelengths during one imaging frame period, for all the points in a speckle reduction member application region.

12. The endoscope light source device according to claim 11, wherein
the speckle reduction member moves by a distance of $5 \times \lambda_{long}$ or more during the one imaging frame period, in a point having a shortest moving distance with respect to the speckle reduction member application region.

13. The endoscope light source device according to claim 12, wherein
the speckle reduction member moves by a distance equal to or larger than an average unevenness interval of a standard quality grade glass during the one imaging frame period, in the point having the shortest moving distance with respect to the speckle reduction member application region.

14. The endoscope light source device according to claim 13, wherein
the driver moves the speckle reduction member so that the speckle reduction member performs rotation movement, swing movement, or shaking movement.

15. An endoscope device comprising:
an endoscope including a light guide; and
the endoscope light source device according to claim 1.

* * * * *